(12) United States Patent
Iguchi et al.

(10) Patent No.: US 10,384,075 B2
(45) Date of Patent: Aug. 20, 2019

(54) LIGHT IRRADIATION SUBSTRATE

(71) Applicant: SHARP KABUSHIKI KAISHA, Sakai, Osaka (JP)

(72) Inventors: Katsuji Iguchi, Sakai (JP); Jun Mori, Sakai (JP); Tohru Nakanishi, Sakai (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 67 days.

(21) Appl. No.: 15/553,583

(22) PCT Filed: Feb. 15, 2016

(86) PCT No.: PCT/JP2016/054291
§ 371 (c)(1),
(2) Date: Aug. 25, 2017

(87) PCT Pub. No.: WO2016/136519
PCT Pub. Date: Sep. 1, 2016

(65) Prior Publication Data
US 2018/0178034 A1   Jun. 28, 2018

(30) Foreign Application Priority Data
Feb. 27, 2015   (JP) .................................. 2015-039306

(51) Int. Cl.
*A61N 5/06* (2006.01)
(52) U.S. Cl.
CPC ......... *A61N 5/0624* (2013.01); *A61N 5/0616* (2013.01); *A61N 2005/0626* (2013.01);
(Continued)

(58) Field of Classification Search
CPC ...... A61N 5/0624; A61N 5/0616; A61N 5/06; A61N 2005/0663; A61N 2005/0652;
(Continued)

(56) References Cited

U.S. PATENT DOCUMENTS 5,616,140 A * 4/1997 Prescott ................... A61N 5/06
606/10
5,913,883 A   6/1999 Alexander et al.
(Continued)

FOREIGN PATENT DOCUMENTS

CN   101050846 A   10/2007
CN   103247740 A   8/2013
(Continued)

OTHER PUBLICATIONS

Kuniyuki Morimoto, et al., 'Photodynamic Therapy Using Systemic Administration of 5-Aminolevulinic Acid and a 410-nm Wavelength Light-Emitting Diode for Methicillin-Resistant *Staphylococcus aureus*-Infected Ulcers in Mice', PLOS ONE, Aug. 2014, vol. 9, Issue 8 e105173.

Primary Examiner — Catherine M Voorhees
(74) Attorney, Agent, or Firm — ScienBiziP, P.C.

(57) ABSTRACT

A light irradiation substrate (1) includes a flexible substrate (5), first electrical conducting material patterns (15) composed of wirings (2) and a dummy pattern (6) which are provided on a front surface of the flexible substrate (5), and LED chips (4) each of which is mounted on each of the wirings (2), front surfaces of the first electrical conducting material patterns (15) are formed of a reflecting material having total light flux reflectance of 80% or more, and area coverage of the first electrical conducting material patterns (15) at least in a region surrounded by the LED chips (4) is 85% or more.

7 Claims, 18 Drawing Sheets

(52) U.S. Cl.
CPC ............. *A61N 2005/0632* (2013.01); *A61N 2005/0643* (2013.01); *A61N 2005/0652* (2013.01); *A61N 2005/0662* (2013.01); *A61N 2005/0663* (2013.01)

(58) Field of Classification Search
CPC .... A61N 2005/0643; A61N 2005/0632; A61N 2005/0662; A61N 2005/062; B41J 2/45
See application file for complete search history.

(56) References Cited

U.S. PATENT DOCUMENTS

| | | | |
|---|---|---|---|
| 6,096,066 A * | 8/2000 | Chen ................. | A61N 5/062 607/88 |
| 6,290,713 B1 * | 9/2001 | Russell .............. | A61N 5/0616 607/88 |
| 2004/0111132 A1 * | 6/2004 | Shenderova ........ | A61N 5/0616 607/88 |
| 2010/0106077 A1 | 4/2010 | Rabin et al. | |
| 2013/0144364 A1 | 6/2013 | Wagenaar et al. | |

FOREIGN PATENT DOCUMENTS

| | | |
|---|---|---|
| JP | 2003-507144 A | 2/2003 |
| JP | 2011-228463 A | 11/2011 |
| JP | 2013-171853 A | 9/2013 |
| WO | 0114012 A1 | 3/2001 |
| WO | 2008144157 A1 | 11/2008 |
| WO | 2012023086 A1 | 2/2012 |

* cited by examiner

LIGHT IRRADIATION SUBSTRATE

TECHNICAL FIELD

The present invention relates to a light-emitting substrate for light irradiation which is used for phototherapy, hairdressing, or cosmetics to irradiate mainly an affected part of a skin of a human being or an animal with light.

BACKGROUND ART

Phototherapy is utilized for various objects including treatment for a disease such as neonatal jaundice, psoriasis, or acne, alleviation of pain, and cosmetics. Green light and blue-white light are used for treatment for neonatal jaundice, ultraviolet light is used for treatment for psoriasis, and blue light, red light, and yellow light are used for treatment for acne. In this manner, various light sources are used in accordance with uses.

In NPL 1, a therapeutic method for methicillin-resistant *staphylococcus aureus* (hereinafter, referred to as "MRSA") infected skin ulcer using near ultraviolet light is described. The therapeutic method is a method in which a part infected with *staphylococcus aureus* having antibiotic resistance is irradiated with near ultraviolet light (wavelength of about 410 nm) to thereby annihilate the bacteria, and is based on a process in which 5-aminolevulinic acid (hereinafter, referred to as "ALA") subjected to systemic administration is, in the bacteria, metabolized to protoporphyrin IX (hereinafter, referred to as "PpIX") and accumulated, and the bacteria is destroyed from an inside of the bacteria by active oxygen generated when the PpIX is decomposed by near ultraviolet light.

It is considered that the therapeutic method has a wide application range and highly promising as a technique by which a side effect is not caused to a cell itself in an affected part at all and which enables killing of a bacteria having antibiotic resistance without causing contamination by an antibiotic substance.

In order to spread such a technique, a light irradiation device that is able to uniformly radiate light to affected parts having various three-dimensional shapes and sizes is required.

Conventionally, a device using a light source such as an excimer lamp or an arc lamp, a device using a laser as a light source, a device of a system in which therapeutic light is radiated planarly by using an optical fiber, and the like have been known as the light irradiation device, for example.

CITATION LIST

Patent Literature

PTL 1: U.S. Pat. No. 5,616,140 (registered on Apr. 1, 1997)
PTL 2: U.S. Pat. No. 5,913,883 (registered on Jun. 22, 1999)
PTL 3: International Publication No. WO2001/014012A1 (internationally published on Mar. 1, 2001)
PTL 4: International Publication No. WO2008/144157A1 (internationally published on Nov. 27, 2008)
PTL 5: International Publication No. WO2012/023086A1 (internationally published on Feb. 23, 2012)

Non Patent Literature

NPL 1: Kuniyuki Morimoto and other six people, "Photodynamic Therapy Using systemic Administration of 5-Aminolevulinic Acid and a 410-nm Wavelength Light-Emitting Diode for Methicillin-Resistant *Staphylococcus aureus*-Infected Ulcers in Mice", PLCS ONE, August 2014, Volume 9, Issue 8 e105173, (published on Aug. 20, 2014)

SUMMARY OF INVENTION

Technical Problem

However, the above-described conventional techniques have problems described below.

For example, in the case of a light source such as the excimer lamp or the arc lamp, therapeutic light is radiated to an affected part arranged at a constant distance from the fixed light source.

However, affected parts to which phototherapy is applied have various shapes, sizes, and areas. Particularly, in a case where phototherapy is applied to a topical disease having a relatively small area of about several cm, when such a light source of a lamp type is used, an irradiation area is too large and a part other than an affected part is irradiated with therapeutic light, so that there is a concern about various side effects on a normal part. Thus, some shielding counter measures need to be taken to prevent irradiation to the normal part with therapeutic light, and the therapy takes time and effort. For example, in a case where a disease developed in a part of a face is treated, a mask for eyes (blindfold) with which eyes that are normal parts are protected is necessary, and, furthermore, a mask which exposes only an affected part of the face is necessary in order to protect normal parts of the face. Moreover, for the treatment, a patient is required to keep his/her posture without moving for several tens of minutes in a state where his/her body is restrained, and such an experience is not pleasant even for the treatment. In a case where an affected part has a curved surface, for example, as an arm or a foot, the irradiation device of the lamp type may force a patient to take an unnatural posture depending on a part such as a front, a rear, or a side. In addition, irradiation intensity is different for each position of the affected part in accordance with an angle or a distance of the affected part having the curved part with respect to the lamp, so that it is difficult to irradiate the entirety of the affected part with uniform therapeutic light in some cases. Further, the device using such a light source of the lamp type has many accompanying devices such as a power source and a cooling device and is large-sized, so that a large space is required for installation and a price of the device becomes high. Thus, only a therapeutic facility is able to install the device, and it is necessary to go to the facility regularly.

On the other hand, in the device using the laser as a light source, since irradiation light thereof is spot light whose irradiation area is small, scanning by the spot light is necessary for irradiation to the entirety of an affected part having a large area with therapeutic light, so that the device becomes complicated and expensive.

Moreover, in the device of the system in which therapeutic light is radiated planarly by using the optical fiber, since efficiency of sending light to the optical fiber is relatively low, irradiation power cannot be prevented from becoming low, so that the device is suitable only for treatment for a relatively long time.

Then, a flexible substrate which is able to keep a constant distance from an affected part and cover the affected part along a shape of the affected part and includes a light source has been demanded.

Note that, for such a demand, some techniques described below have been proposed. PTL 1 discloses a light irradiation device in which a laser and an LED each serving as a light-emitting light source are arranged on a flexible substrate and which is used by being wound around an affected part. However, PTL 1 does not include specific disclosure about performing efficient and uniform light irradiation to an affected part. PTL 2 discloses a light irradiation device for a face in which an LED serving as a light-emitting light source is arranged on a flexible substrate and which is used by covering a face. However, PTL 2 does not include specific disclosure about performing efficient and uniform light irradiation to a limited affected part. PTL 3 discloses a flexible light irradiation device in which a large number of LEDs each serving as a light-emitting light source are arranged on a flexible substrate and which performs light irradiation with the flexible substrate wound around an affected part. However, a structure disclosed in PTL 3 is heavy and thick, and not suitable for treatment for a topical affected part on a skin. PTL 3 does not include specific disclosure about performing efficient and uniform light irradiation. PTL 4 discloses a light irradiation device in which an LED serving as a light-emitting light source is arranged inside a cap, on the assumption that the light irradiation device is applied to a head. However, PTL 4 does not include specific disclosure about performing efficient and uniform, light irradiation to a limited affected part. PTL 5 discloses a light irradiation device in which an LED serving as a light-emitting light source is arranged on a flexible substrate and a light-transmitting material is held between an affected part and the LED so that light emitted from the LED is able to be transmitted to the affected part. However, in the light irradiation device of PTL 5, an air layer lies between the affected part and the LED, and efficiency of light irradiation is therefore deteriorated, PTL 5 does not include specific disclosure about performing uniform light irradiation to a topical affected part while enhancing efficiency of light irradiation.

In addition, none of the techniques is realized or in a situation of being widely used.

Each of PTLs 1 to 5 enables covering of an affected part along a shape of the affected part by covering the affected part with a flexible substrate in which an LED is provided. However, irradiation intensity is different for each position of the affected part in accordance with an angle or a distance of the affected part having a curved part with respect to the light source, so that it is difficult to irradiate the entirety of the affected part with uniform therapeutic light. Particularly, in order to make a patient less restrained and suppress a burden of the patient to a minimum, it is important to realize light irradiation which suppresses a loss of light to a minimum, improves intensity of irradiation light, and is almost uniform and efficient, but it is difficult to say that each of the techniques of PTLs 1 to 5 is able to realize the almost uniform and efficient light irradiation.

The invention is made in view of the aforementioned problems, and an object thereof is to provide a light irradiation substrate that is suitable for treatment for a relatively small diseased part and is capable of realizing almost uniform and efficient light irradiation to the entirety of an affected part even when the affected part is not flat.

Solution to Problem

In order to solve the aforementioned problems, a light irradiation substrate according to an aspect of the invention includes: a flexible substrate that is insulating; first electrical conducting material patterns that are provided on a first surface of the flexible substrate; and light-emitting elements that are mounted on at least a part of the first electrical conducting material patterns, in which front surfaces of the first electrical conducting material patterns are formed of a reflecting material with total light flux reflectance percentage of 80% or more, and area coverage of the first electrical conducting material patterns at least in a region surrounded by the light-emitting elements is 85% or more.

Advantageous Effects of Invention

According to an aspect of the invention, it is possible to provide a light irradiation substrate that is suitable for treatment for a relatively small diseased part and is capable of realizing almost uniform and efficient light irradiation even of am affected part which is not flat. According to an aspect of the invention, it is possible to realize efficient and uniform light irradiation while suppressing a side effect caused by the light irradiation to a minimum, so that it is possible to realize an effect of phototherapy with which a burden of a patient and his/her family is suppressed.

DESCRIPTION OF EMBODIMENTS

Hereinafter, embodiments of the invention will be described in detail. Note that, dimensions, materials, shapes, relative positions, processing processes, and the like of constituents described in the embodiments below merely exemplify an embodiment, and should not be considered as limiting the scope of the invention only to them. Furthermore, drawings are schematically illustrated, and ratios between dimensions and shapes are different from actual ones.

Embodiment 1

An embodiment of the invention will be described as follows on the basis of FIG. 1 to FIG. 6. Note that, description below will be given by setting that a surface of a light irradiation substrate, onto which an LED (light-emitting diode) chip is mounted, is a front surface (first surface) and a surface opposite to the surface onto which the LED chip is mounted is a rear surface (second surface).

Figure 1:
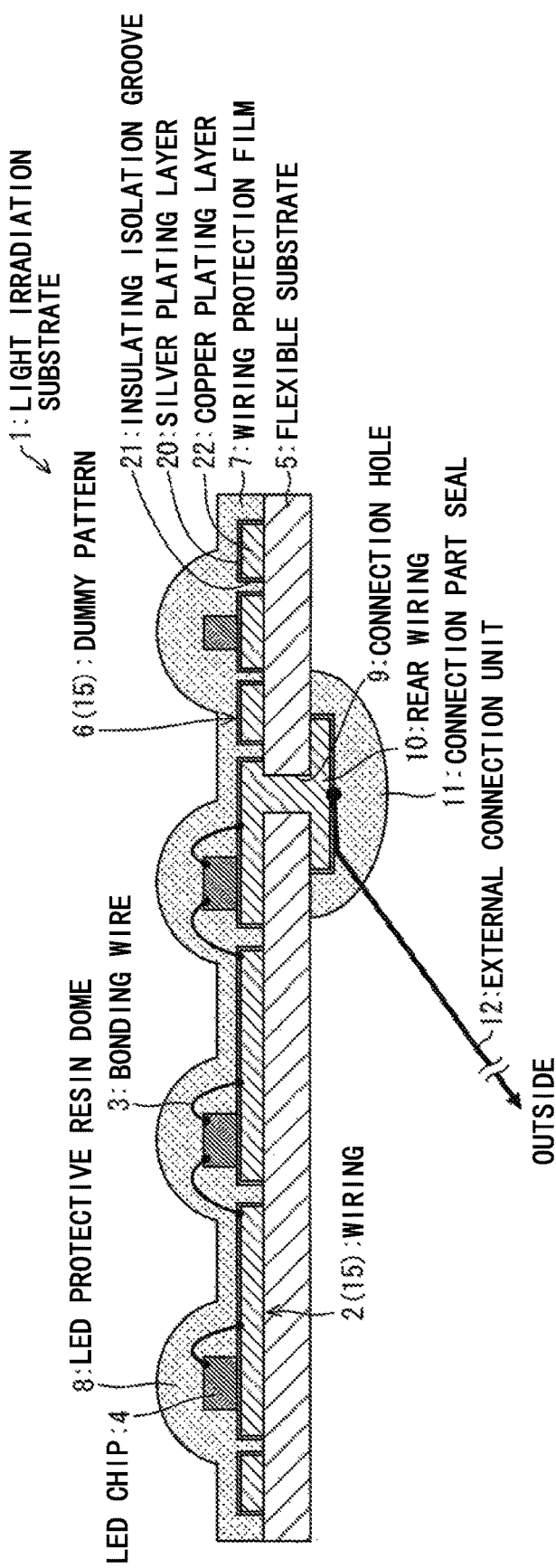
FIG. 1 is a schematic sectional view illustrating a configuration of a light irradiation substrate according to Embodiment 1 of the invention.
Figure 2:
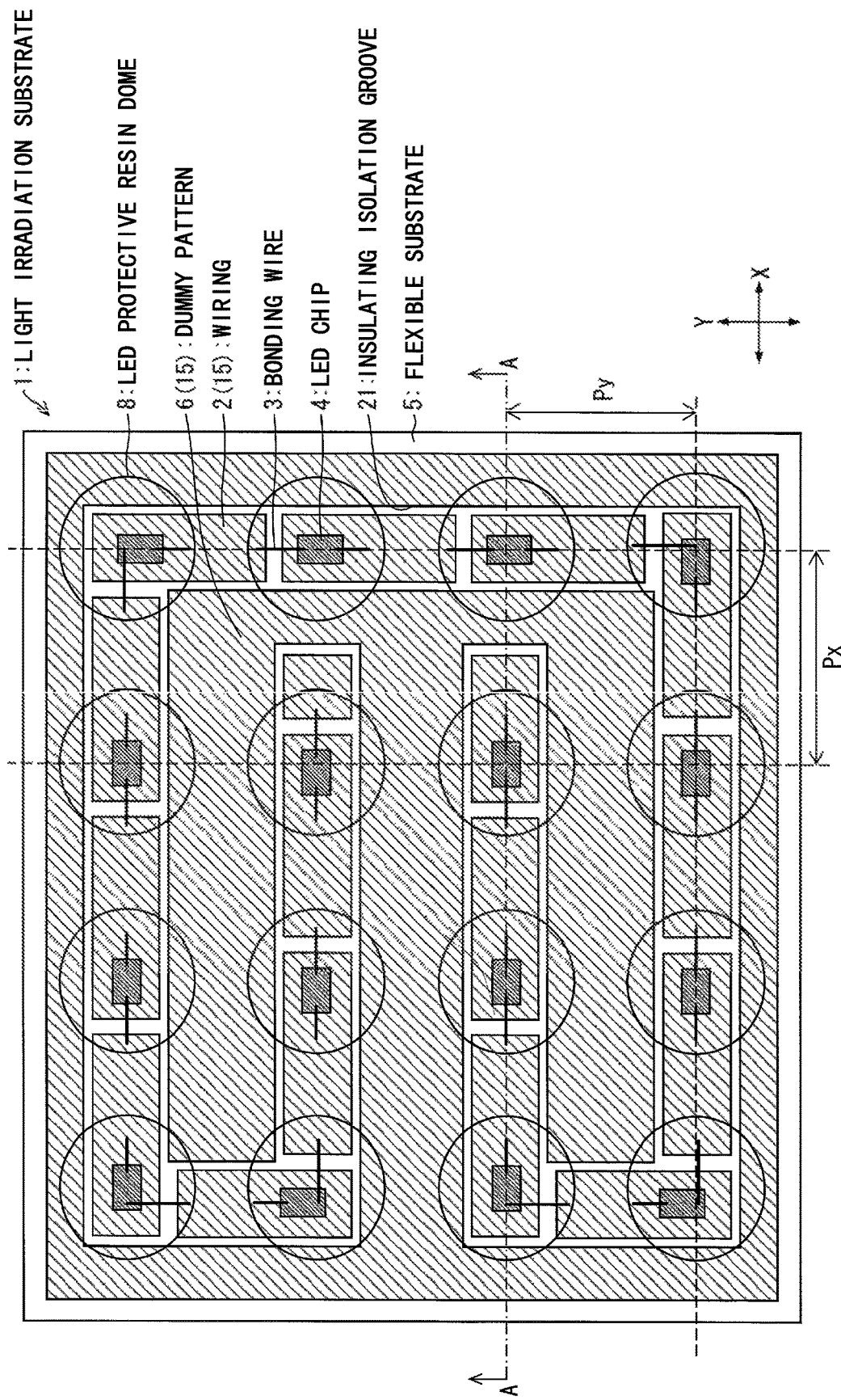
FIG. 2 is a schematic front surface view illustrating the configuration of the light irradiation substrate according to Embodiment 1 of the invention.
Figure 3:
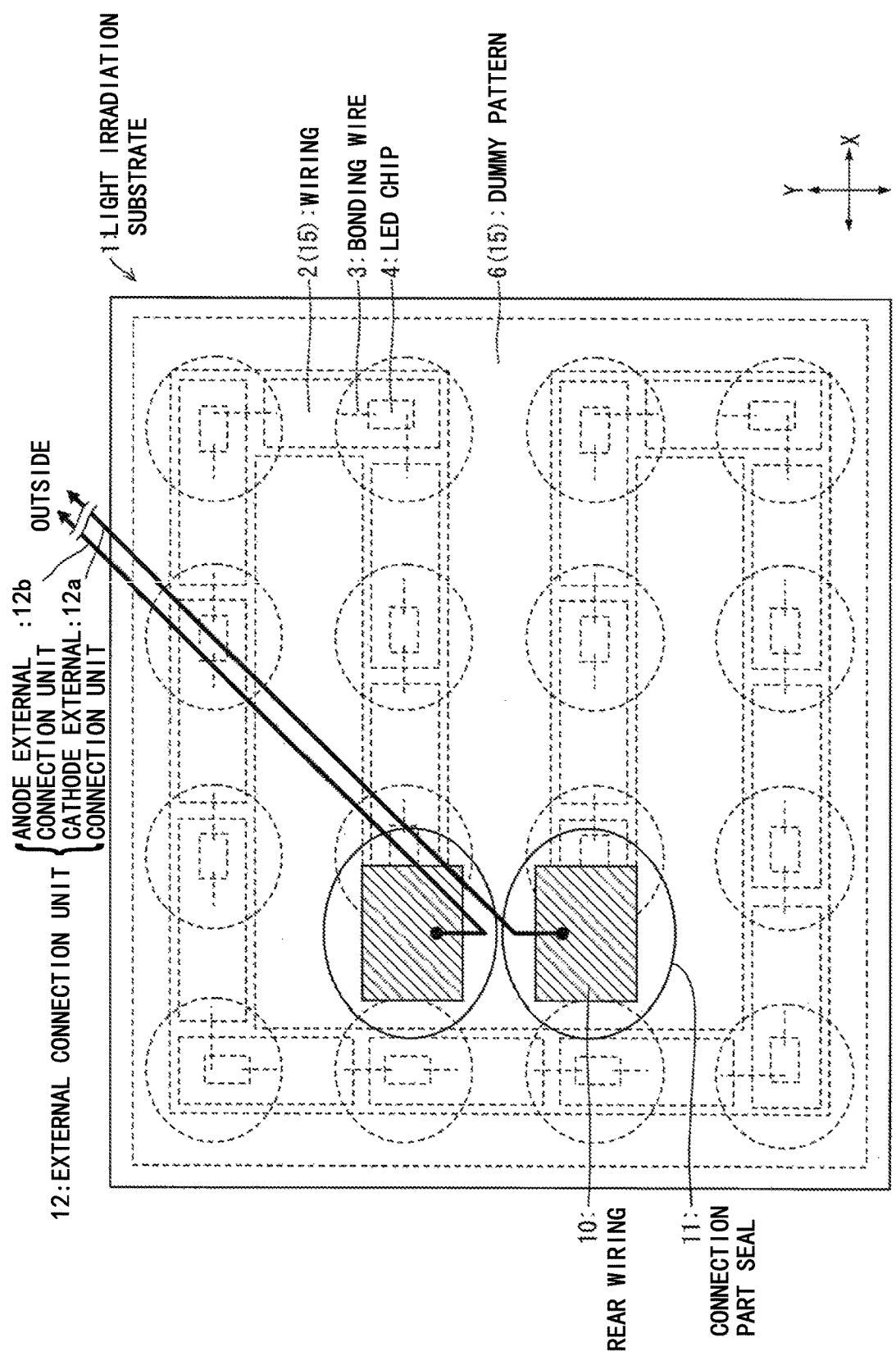
FIG. 3 is a schematic rear surface view illustrating the configuration of the light irradiation substrate according to Embodiment 1 of the invention.

FIG. 1 is a sectional view schematically illustrating a configuration of a light irradiation substrate 1 according to the present embodiment. FIG. 2 is a schematic front surface view illustrating the configuration of the light irradiation substrate 1 according to the present embodiment. FIG. 3 is a schematic rear surface view illustrating the configuration of the light irradiation substrate 1 according to the present embodiment.

FIG. 1 corresponds to a sectional view taken along an A-A line of the light irradiation substrate 1, which is illustrated in FIG. 2. Note that, for convenience of illustration, illustration of a wiring protection film 7 is omitted in FIG. 2.
(Schematic Configuration of Light Irradiation Substrate 1)

First, a schematic configuration of the light irradiation substrate 1 will be described.

As illustrated in FIG. 1 to FIG. 3, the light irradiation substrate 1 includes a flexible substrate 5, a plurality of wirings 2 (wiring patterns, first surface side wirings) each of which is insulated and isolated by an insulating isolation groove 21, a dummy pattern 6, a plurality of LED chips 4 (light-emitting elements), a plurality of bonding wires 3, the wiring protection film 7, a plurality of LED protective resin domes 8, a plurality of rear wirings 10 (wiring patterns, second surface side wirings), a connection part seal 11, and an external connection unit 12.

The wirings 2 and the dummy pattern 6 are formed on one main surface (front surface, first surface) of the flexible substrate 5. The insulating isolation groove 21 is formed in a space between each of the wirings 2 and the dummy pattern 6, and each of the wirings 2 and the dummy pattern 6 are insulated and isolated by the insulating isolation groove 21.

Each of the LED chips 4, which serves as a light source, is mounted on each of the wirings 2. The wirings 2 are insulated and isolated by the insulating isolation groove 21, and one LED chip 4 is mounted on one wiring 2. The LED chips 4 are connected in series. Each of the LED chips 4 is connected by the bonding wires 3 to a wiring 2 on which the LED chip 4 is mounted and to another wiring 2 which is adjacent to the wiring 2 via the insulating isolation groove 21.

Among the LED chips 4 and the bonding wires 3, each of the LED chips 4 and the bonding wires 3 connected to the LED chip 4 are covered with each of the LED protective resin domes 8 which serve as protection films. Moreover, a part of the front surface of the flexible substrate 5, which is not covered with the LED protective resin domes 8, is covered with the wiring protection film 7 serving as a protection film covering the wirings 2 and the dummy pattern 6.

On the other hand, the rear wirings 10 are formed on the other main surface (rear surface, second surface) of the flexible substrate 5. Connection holes 9 each passing through the flexible substrate 5 are provided in the flexible substrate 5. The wirings 2 and the rear wirings 10 are connected via the connection holes 9. Moreover, the wirings 2 are electrically connected to the external connection unit 12 via the rear wirings 10. A wire connection part of the external connection unit 12 and each of the rear wirings 10 is insulated and isolated by the connection part seal 11.

Next, each constituent of the light irradiation substrate 1 will be described in more detail.
(Flexible Substrate 5)

The flexible substrate 5 is an insulating substrate, and is formed of an insulating film, for example, such as polyimide. However, a material of the flexible substrate 5 is not necessarily limited to the polyimide, and any material is able to be used as long as the material is an insulating material and has necessary strength and flexibility. In addition to a polymide resin film, various materials, for example, such as a film of fluororesin, silicon resin, polyethylene terephthalate resin, or the like, a highly reflective resin film obtained by applying resin including a white pigment (white resin, white resist, or the like) to a surface of such a film, and a highly reflective resin film in which a white pigment is mixed are able to be used as the aforementioned flexible substrate 5. A highly reflective material is expensive, but has high reflectivity of light irradiation. For inexpensive transparent resin, a measure against light leaking out to the rear surface of the substrate is required in some cases.

Affected parts to which phototherapy is applied have various shapes, sizes, and areas. Accordingly, neither a size nor a shape of the flexible substrate 5 is particularly limited. The flexible substrate 5 is required only to have a size that allows covering of an affected part, so that, when the light irradiation substrate 1 has a size that allows light irradiation with the only affected part covered, it is possible to make a patient less restrained and suppress a burden of the patient to a minimum.

The light irradiation substrate 1 is suitably used for a topical disease having a relatively small area of about several cm. It is desired that the flexible substrate 5 is formed so as to have a size corresponding to the topical disease.

A thickness of the flexible substrate 5 is not particularly limited as long as necessary strength and flexibility are provided. In the present embodiment, a film having a thickness of 50 μm is used, but may certainly have a different thickness.

(Wiring 2 and Dummy Pattern 6)

The wirings 2 each of which is formed of a copper-plating layer 22 (copper plating wiring, first electrical conducting material) whose front surface is covered with a silver plating layer 20 are formed on the flexible substrate 5.

A part of the front surface of the flexible substrate 5, which is not covered with the wirings 2 is covered with the dummy pattern 6, except for the insulating isolation groove 21 that is necessary for insulation and isolation between the adjacent wirings 2 and between each of the wirings 2 and the dummy pattern 6.

The dummy pattern 6 is formed of the same material (first electrical conducting material) as that of each of the wirings 2, and the dummy pattern 6 and the wirings 2 are formed on the same surface of the flexible substrate 5 at the same time with the use of the same material.

The dummy pattern 6 and the wirings 2 are able to be formed, for example, by applying copper plating to the front surface of the flexible substrate 5 formed of a polyimide film, forming the insulating isolation groove 21 to thereby form the copper plating layer 22 which has been patterned, and applying silver plating to a front surface of the copper plating layer 22. Thus, the dummy pattern 6 is formed of the copper plating layer 22 whose front surface is covered with the silver plating layer 20 in the same manner as the wirings 2.

Figure 5:
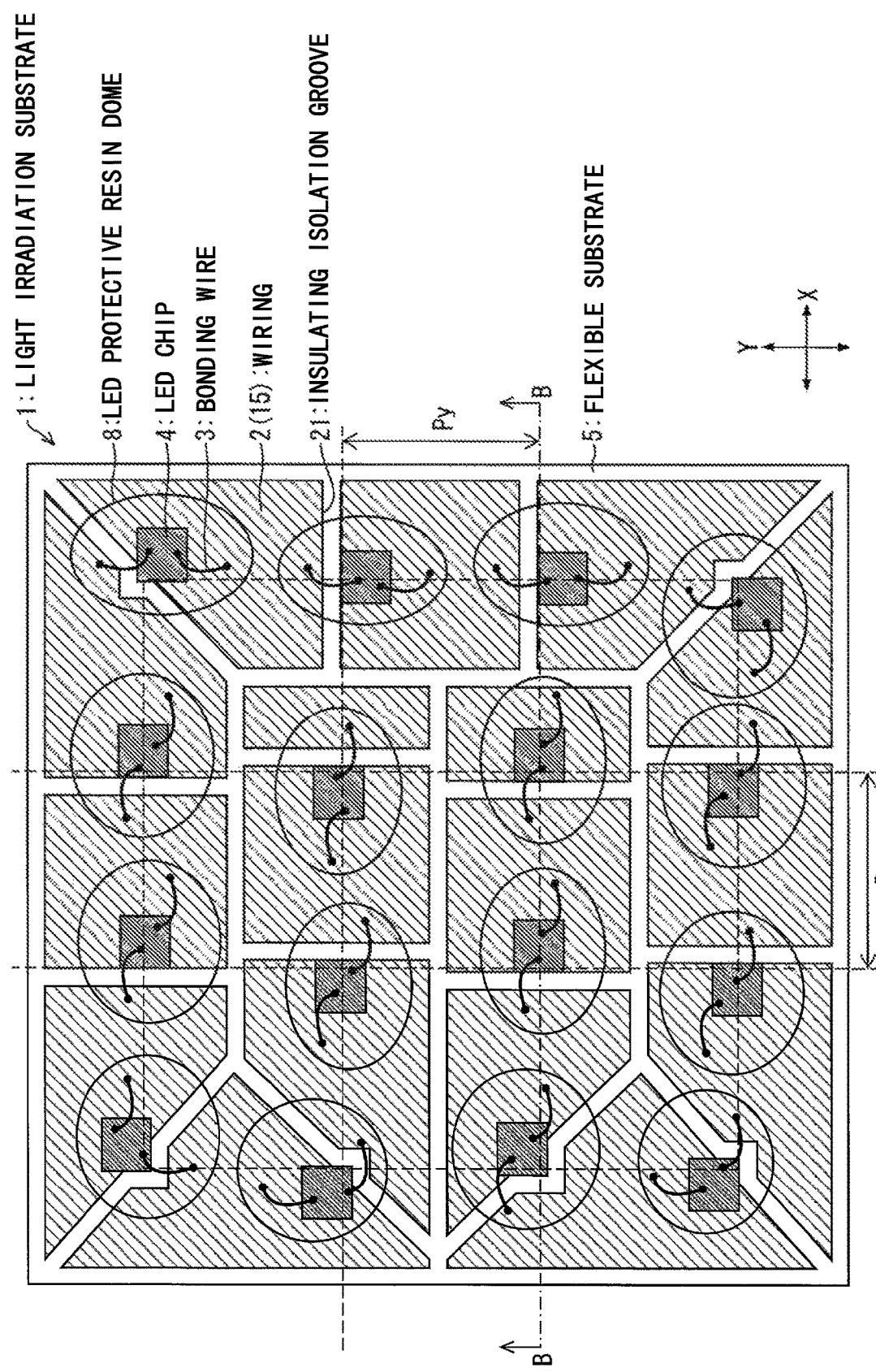
FIG. 5 is a schematic front surface view illustrating another configuration of the light irradiation substrate according to Embodiment 1 of the invention.
Figure 6:
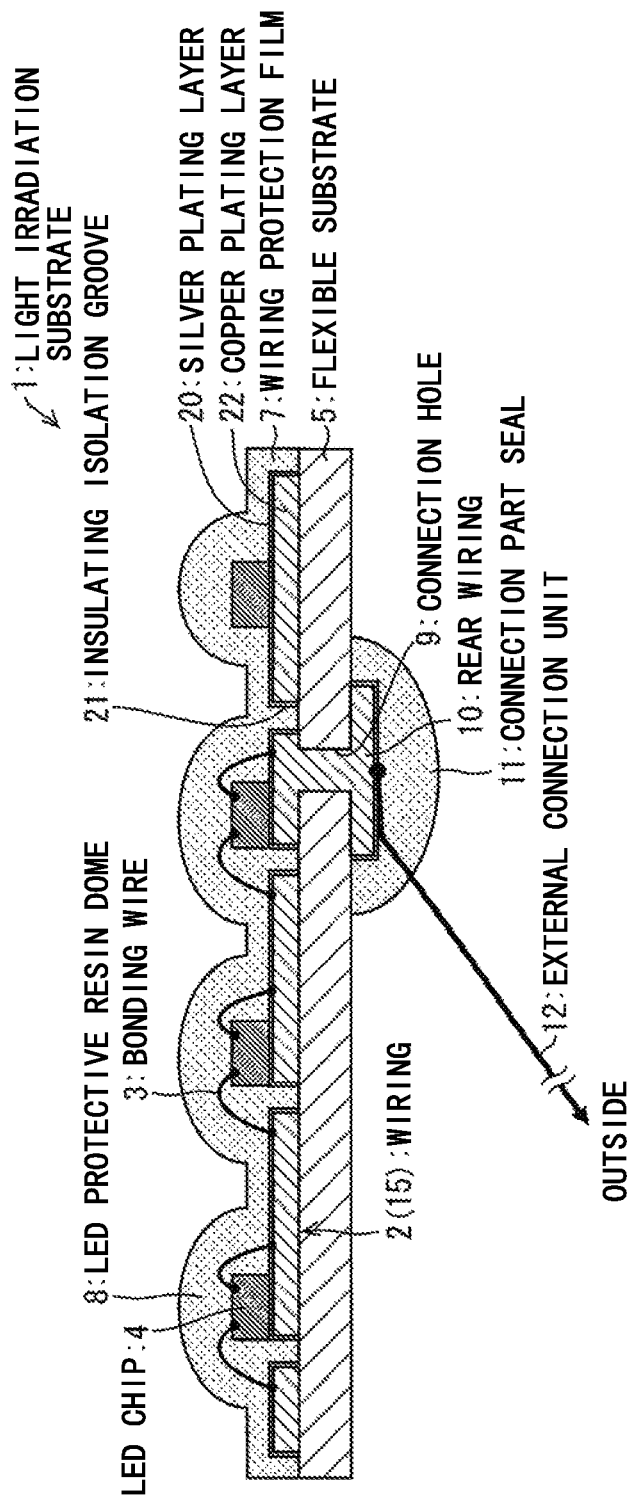
FIG. 6 is a schematic sectional view illustrating the configuration of the light irradiation substrate illustrated in FIG. 5.

However, the dummy pattern 6 is not always necessary. FIG. 5 is a schematic front surface view illustrating another configuration of the light irradiation substrate 1 according to the present embodiment. FIG. 6 is a schematic sectional view illustrating the configuration of the light irradiation substrate 1 illustrated in FIG. 5.

As illustrated in FIG. 5 and FIG. 6, it is also possible to cover the entire front surface of the flexible substrate 5, excluding the insulating isolation groove 21 and an outer periphery of the flexible substrate 5, with the wirings 2 (first surface side wirings).

A material of the wirings is required to have a low resistance and have high reflectance of front surfaces thereof. Particularly, in order to reduce a loss at during light irradiation, it is necessary to minimize an energy loss due to reflection. Thus, total light flux reflectance needs to be at least 80%, and desirably 90% or more.

In this case, the total light flux reflectance does not mean reflectance of specular reflection but a ratio of light energy obtained by integrating all reflected light, which is diffused and reflected, to energy of entering light.

Accordingly, at least for the front surfaces of the wirings 2 on a front side of the flexible substrate 5, a reflecting material having total light flux reflectance of 80% or more (hereinafter, referred to as "high reflectance material"), desirably a high reflectance material having total light flux reflectance of 90% or more is used so that light reflected by an affected part is reflected as much as possible to be returned to the affected part and a loss of light is suppressed to a minimum.

In a case where the wirings 2 do not have the silver plating layer 20 on the front surfaces thereof, there are some cases that light absorption by the copper plating layer 22 is caused and light irradiation time becomes 1.2 times longer.

For the same reason as the wirings 2, the same material as that of the wirings 2 is used for the dummy pattern 6. Moreover, in a case where the dummy pattern 6 is not included, light leaks out to a rear surface side of the dummy pattern 6 through a part in which there is no wiring 2 of the flexible substrate 5, so that there are some cases that the light irradiation time is extended to 1.2 times.

Note that, for the aforementioned high reflectance material, a material of regular reflection may be used, or a material of diffuse reflection may be used. In the present embodiment, copper wirings which are formed of the copper plating layer 22 to the front surface of which the silver plating is applied are used as the wirings 2 as described above, but a material such as aluminum may be used for the wirings 2 or the front surfaces of the wirings 2, for example.

Hereinafter, a wiring pattern formed by the wirings 2 and the dummy pattern 6 are referred to as first electrical conducting material patterns 15 generically.

In the present embodiment, for improving efficiency of light irradiation, it is important that the first electrical conducting material patterns 15 cover the front surface of the flexible substrate 5 over an area as large as possible. In FIG. 2, when it is set that each pitch between the LED chips 4 that are adjacent to each other in an X direction is Px and each pitch between the LED chips 4 that are adjacent to each other in a Y direction which is orthogonal to the X direction is Py, Px=Py=5 mm is provided. In a case where the first electrical conducting material patterns 15 in which a width of each of the wirings 2 is 1 mm and a width of the insulating isolation, groove 21 is 0.1 mm are used, coverage of the first electrical conducting material patterns 15 at least in a region surrounded by the LED chips 4 on the front surface of the flexible substrate 5 is about 93% to 95%, although there is a difference between places to some extent depending on a pattern, on the flexible substrate 5. Note that, the coverage of the first electrical conducting material patterns 15 here means an area ratio (area coverage) of a region, which is covered with the first electrical conducting material patterns 15, in a target area (for example, an area in the region surrounded by the LED chips 4 on the front surface of the flexible substrate 5, as described above).

On the other hand, when the first electrical conducting material patterns 15 provided under the same condition as those of FIG. 1 and FIG. 2 are used in FIG. 5, the area coverage of the first electrical conducting material patterns 15 at least in the region surrounded by the LED chips 4 on the front surface of the flexible substrate 5 is about 95% to 97%.

Note that, the coverage of the first electrical conducting material patterns 15 does not greatly vary whether or not the dummy pattern 6 is used. However, in a case where the dummy pattern 6 is not used as in FIG. 5, when a defect occurs in any one place of the insulating isolation groove 21, wiring short circuit is generated to cause failure. Whereas, in a case where the dummy pattern 6 is used as in FIG. 2, failure is rarely caused due to a defect in any one place. Thus, the configuration illustrated in FIG. 2 has an advantage that improve a production yield is able to be improved substantially. For example, in a case where, with respect to failure that is caused because there is short circuit failure at one place in the light irradiation substrate 1, the yield when the dummy pattern 6 is provided is 99%, the yield when the dummy pattern 6 is not provided is 48%.

When the width of the insulating isolation groove 21 is widened up to 0.2 mm in order to improve the production yield of the light irradiation substrate 1, the coverage of the first electrical conducting material patterns 15 is about 87% to 91% when the dummy pattern 6 is provided, and 90% to 94% when the dummy pattern 6 is not provided. Although it is important to increase the coverage of the first electrical conducting material patterns 15 in order to improve efficiency of light irradiation by the light irradiation substrate 1, high coverage causes reduction in the yield due to a defect at a time of manufacture, and becomes a factor in increasing costs.

Moreover, trade-off of costs is caused with respect to performance, so that it is necessary to optimize the first electrical conductive material patterns 15 in accordance with a purpose of use. Then, the coverage (area coverage) of the first electrical conducting material patterns 15 at least in the region surrounded by the LED chips 4 on the front surface of the flexible substrate 5 is preferably 85% or more, and more preferably 90% or more.

(LED Chip 4 and Bonding Wire 3)

It is necessary to select the LED chip 4 in accordance with an object of treatment. Here, for application to "therapy for methicillin-resistant *staphylococcus aureus* (MRSA) infected skin ulcer (refer to NPL 1)", a gallium nitride based blue-violet LED (peak wavelength of 410 nm) is used for the LED chip 4. For other uses, it is possible to select, as the LED chip 4, an optimum LED in accordance with an object from an ultraviolet LED, a blue LED, a green LED each of which is the gallium nitride (AlInGaN) LED the same as the blue-violet LED, red, yellow, and green LEDs of quaternary system. (AlGaInP) LEDs, a GaAs based infrared LED, and the like. Note that, it is also possible to combine, as the LED chip 4, a plurality of LEDs whose wavelength bands are different.

In order to uniformly perform light irradiation to an affected part having a constant size as in phototherapy, arranging a large number of LED chips 4 which are relatively small is better than using a small number of high-power LED chips 4. In the present embodiment, 16 blue-violet LED chips each of which has a size of 440 μm×550 μm are mounted on the flexible substrate 5 as the LED chips 4.

As illustrated in FIG. 2 and FIG. 3, the LED chips 4 are arranged in a two-dimensional array in which four pieces× four pieces are respectively arrayed along the X direction (first direction) and the Y direction (second direction) which is in the same plane as the X direction and orthogonal to the X direction. When it is set that each pitch between the LED chips 4 that are adjacent to each other in the X direction is Px and each pitch between the LED chips 4 that are adjacent to each other in the Y direction which is orthogonal to the X direction is Py as illustrated in FIG. 2, the LED chips 4 are arranged in the two-dimensional array at almost constant pitch (Px, Py).

Note that, the X direction and the Y direction here are array directions of the LED chips 4, and, in the present embodiment, the LED chips 4 are arrayed in parallel to each side of the flexible substrate 5 that is in a rectangular shape (for example, a square shape). Moreover, the pitch between the LED chips 4 that are adjacent to each other in the X direction or the Y direction means a distance between the centers of the LED chips 4 that are adjacent to each other in the X direction or the Y direction.

In this manner, by arranging the LED chips 4 in the two-dimensional array at almost constant pitch (Px, Py) in an inside of the light irradiation substrate 1, it is possible to improve uniformity of intensity of light irradiation in the inside of the light irradiation substrate 1.

Note that, although Px=Py is satisfied generally, light output distribution is different between the X direction and the Y direction depending on shapes of the LED chips 4 in some cases. In this case, it is desired that the pitches (Px, Py) between the LED chips 4 are made different between the X direction and the Y direction. For example, in an LED chip 4 that has a long and narrow shape, there is a tendency that light is easily output in a direction perpendicular to a long side thereof and a little light is output in a direction perpendicular to a short side thereof. In a case where the long side of the LED chip 4 is, for example, parallel to the X direction, it is desired that Px<Py is satisfied. In order to achieve the simplest array, it is desired that the LED chip 4 whose shape is nearly a square is used and Px=Py is satisfied. Note that, the above-described tendency is affected by arrangement of electrodes of the LED chip 4 in some cases. Accordingly, it is desired that optimization is performed in accordance with actual light-emitting characteristics of the LED chip 4.

In the present embodiment, am average pitch between the LED chips 4 is set to be about 5 mm to 10 mm. As the LED chips 4 having such a size, LED chips each having the most common structure in which a nitride semiconductor layer is grown epitaxially on a sapphire substrate and a cathode electrode and an anode electrode are formed on the same plane have the best light-emitting efficiency.

In the present embodiment, each of the above-described LED chips 4 in each of which the cathode electrode and the anode electrode are formed on the same plane is bonded onto each of the wirings 2 with transparent die bond paste. The cathode electrode and the anode electrode of the LED chip 4, which are not illustrated, are connected (wired) to the wiring 2 with the bonding wires 3 as illustrated in FIG. 1 to FIG. 3.

For the bonding wire 3, gold (gold bonding wire) is used. However, the bonding wire 3 is not necessarily formed of gold, and a publicly known bonding wire formed of silver, aluminum, or the like may be used.

Note that, in a case where a quaternary system (AlGaInP) LED or a GaAs infrared LED is used as the LED chip 4 at a time of treatment, the LED chip 4 has a so-called vertical electrode structure. Therefore, in a case where the LED chip 4 in which the cathode electrode and the anode electrode have the vertical electrode structure in this manner is used, a lower surface of the LED chip 4, which serves as a lower electrode of the LED chip 4, is to be bonded onto the wiring 2 with am electrical conducting material such as silver paste and an upper electrode is to be bonded onto the wiring 2, which is different from the wiring 2 onto which the LED chip 4 is mounted, with the bonding wire 3.

(LED Protective Resin Dome 8 and Wiring Protection Film 7)

In order to protect the LED chips 4 and the bonding wires 3, the LED chips 4 and the bonding wires 3 are covered with the LED protective resin domes 8 each of which is formed of a resin layer in a dome shape.

Each of the LED protective resin domes 8 is able to be formed by potting, but is better to be resin-molded with the use of a die so as to secure reproducibility of the shape.

In order to prevent the silver plating layer 20 from corroding and secure an insulating property of the front surface of the light irradiation substrate 1, the wiring protection film 7 that covers the first electrical conducting material patterns 15 (the wirings 2 an the dummy pattern 6) is formed on the front surface of the flexible substrate 5 as described above. The wiring protection film 7 is formed on the front surface of the flexible substrate 5, so that short circuit between the wirings 2 is prevented and corroding of the silver is prevented.

Note that, in order to secure flexibility of the light irradiation substrate 1 as much as possible, it is preferable to use resin which is as flexible as possible for the LED protective resin domes 8 and the wiring protection film 7. With hard resin, in a case where the light irradiation substrate 1 is bent, the bonding wire 3 is broken in some cases.

It is desired that the LED protective resin domes 8 and the wiring protection film 7 are formed of the same material (insulating resin), but different materials may be used. In the present embodiment, the wiring protection film 7 is formed by coating the front surface of the flexible substrate 5 with silicone resin so as to cover the first electrical conducting material patterns 15 (the wirings 2 and the dummy pattern 6), and the LED chips 4 and the bonding wires 3 are covered with the silicone resin domes.

(External Connection Unit 12 and Rear Wiring 10)

The external connection unit 12 is a wiring unit by which the light irradiation substrate 1 is connected to an external power source that supplies an electrical current to the light irradiation substrate 1, and supplies electrical power to the LED chips 4 from an outside via the wirings 2.

In the present embodiment, the external connection unit 12 is provided in the rear surface side of the flexible substrate 5 as illustrated in FIG. 1 and FIG. 3. The external connection unit 12 is wired to each of the rear wirings 10 by solder connection or the like. Each of the rear wirings 10 is connected to a part of the wirings 2 on the front side via each of the connection holes 9. The rear wirings 10 and the wirings 2 are electrically connected to each other in this manner, so that the external connection unit 12 is electrically connected to the wirings 2 via the rear wirings 10.

Note that, a spacer 32 (refer to FIG. 4) that keeps a distance to an affected part constant and fixes a positional relation between the light irradiation substrate 1 and the affected part is provided on the front surface side of the light irradiation substrate 1, as described below. It is therefore difficult to provide a wire connection part of the external connection unit 12 to the wirings of the light irradiation substrate 1 on the front surface side of the light irradiation substrate 1.

In a case where the wire connection part is provided on the front surface side of the light irradiation substrate 1, connecting work (soldering) of the external connection unit 12 is required on a formation surface of the LED chips 4 and the wirings 2 after mounting the LED chips 4. Accordingly, when the wire connection part is provided on the front surface side of the light irradiation substrate 1, the production yield of the light irradiation substrate 1 may be lowered, for example, due to reduction in reflectance, which is caused by a stain on the front surface of any of the first electrical conducting material patterns 15 (the wirings 2 and the dummy pattern 6), or short circuit which is caused when dust mounts on the insulating isolation groove 21.

However, according to the present embodiment, by drawing out the external connection unit 12 to the rear surface side of the flexible substrate 5 as described above, it is possible to easily form the wire connection part and avoid the above-described problems.

The external connection unit 12 includes a lead wire, a connector with which the lead wire is connected to the flexible substrate 5, and the like, for example. Moreover, it is preferable that the external connection unit 12 is terminated with a socket, a plug, or the like in order to enhance convenience of connection with the power source and is able to be easily connected to the power source.

Figure 4:
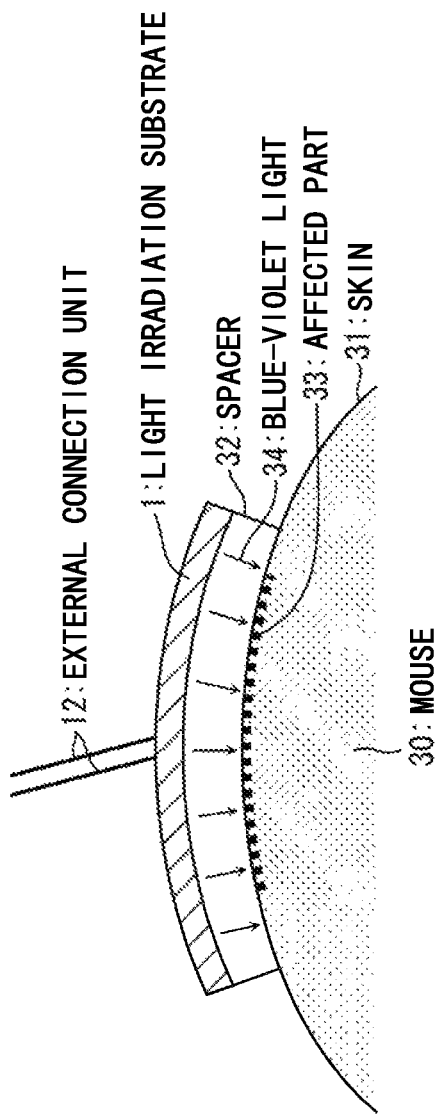
FIG. 4 is a schematic view illustrating an application example in treatment with the light irradiation substrate according to Embodiment 1 of the invention.

Thus, although the lead wire is illustrated as the external connection unit 12 in FIG. 1, FIG. 3, and FIG. 4, this is mere exemplification, and, needless to say, the connector or the like with which the lead wire is connected may be actually provided in the flexible substrate 5.

Moreover, the external connection unit 12 includes a cathode external connection unit 12a and an anode external connection unit 12b as illustrated in FIG. 3. In the present embodiment, since all of the LED chips 4 are connected in series, the wirings 2 are arrayed in a one-stroke pattern so that a wiring end of the wiring 2, which is connected to the rear wiring 10 wired to the cathode external connection unit 12a, and a wiring end of the wiring 2, which is connected to the rear wiring 10 wired to the anode external connection unit 12b, are adjacent to each other as illustrated in FIG. 3.

However, in a case where the number of LED chips 4 is large and a power source voltage becomes too high only with series connection, parallel connection may be used for connection of the LED chips 4. In this case, well-designing of a wiring pattern of the wirings 2 or the wirings 2 and the rear wirings 10 is required so that the same electrical current flows through each of the wirings 2.

It is preferable that each of the rear wirings 10 is covered with the connection part seal 11, which is made of insulating resin, so as to cover the wire connection part of the external connection unit 12 and the rear wiring 10. By covering each of the rear wirings 10 (wire connection parts) with the connection part seal 11, it is possible to insulate and isolate the rear wirings 10 from each other and secure an insulating property of the rear surface of the light irradiation substrate 1.

Moreover, between the first electrical conducting material patterns 15, the insulating isolation groove 21 is provided as a gap. Thus, in the light irradiation substrate 1, there is a region in which such high reflectance layers (first electrical conducting material patterns 15) formed of a high reflectance material are not provided, and light leaks out albeit slightly to the rear surface side of the flexible substrate 5 through the region.

Then, in order to prevent light from leaking out from the rear surface side of the flexible substrate 5, the rear wirings 10 may be provided so as to cover the insulating isolation groove 21 in a plan view. That is, each of the rear wirings 10 may function also as a light shielding member that prevents light from leaking out from the rear-surface side of the flexible substrate 5.

For example, at a time of applying copper plating and silver plating to the front surface of the flexible substrate 5 which is formed of a polyimide film, copper plating and silver plating are applied also to the rear surface of the flexible substrate 5, so that it is possible to form the rear wirings 10 by the same material as that of the first electrical conducting material patterns 15 and, for example, at the same time.

Thus, the same as the first electrical conducting material patterns 15, the rear wirings 10 are configured by the copper plating layer 22 whose front surface is covered with the silver plating layer 20 in the present embodiment.

Accordingly, by leaving the copper plating layer 22 and the silver plating layer 20 so as to cover the insulating isolation groove 21 (that is, so as to overlap with the insulating isolation groove 21) in a plan view when forming the rear wirings 10 on the rear surface side of the flexible substrate 5, it is possible to reflect light which has been transmitted through the insulating isolation groove 21 by the rear wirings 10 and return the light to an affected part.

Note that, although a case where the rear wirings 10 cover only a part of the insulating isolation groove 21 in a plan view is taken as an example for illustration in FIG. 1, in order to prevent the leakage of light, it is desired that the rear wirings 10 are formed in a range as wide as possible (that is, a part overlapping with the insulating isolation groove 21 as much as possible). However, it is necessary to insulate and isolate the rear wiring 10 wired to the cathode external connection unit 12a and the rear-wiring 10 wired to the anode external connection unit 12b from each other.

Moreover, instead of forming the rear wirings 10 so as to be large as described above, a dummy pattern formed of the same material as that of the rear wirings 10 may be formed also on the rear surface of the flexible substrate 5 at a time of patterning the rear wirings 10. That is, the copper plating layer 22 and the silver plating layer 20 which are applied to the rear surface of the flexible substrate 5 may be left on the rear surface of the flexible substrate 5 as a pattern separated from the rear wirings 10 (that is, connecting parts of the wirings 2 and the external connection unit 12).

Note that, for improving utilization efficiency of light, it is preferable that, as described above, the light shielding member is a reflecting member that reflects light which has been transmitted through the insulating isolation groove 21.

However, as described above, by covering the front-surface of the flexible substrate 5 with the first electrical conducting material patterns 15 as wide as possible, it is possible to return, to an affected part, most of light which has been reflected by the affected part. Although depending on a size of the insulating isolation groove 21, only a little light leaks out from the insulating isolation groove 21 to the rear surface side of the flexible substrate 5. Accordingly, the light shielding member may be a light absorbing member that absorbs light.

For example, in order to prevent the leakage of light, an opaque resin layer that covers the rear surface of the flexible substrate 5 may be provided in the rear surface side of the flexible substrate 5 as the light shielding member. That is, for example, the opaque resin layer may be provided instead of a rear surface reflection film in an embodiment described below. Note that, also in this case, it is desired that the light shielding member is provided so as to cover at least the insulating isolation groove 21 in a plan view in order to absorb light which has been transmitted through the insulating isolation groove 21.

Moreover, in order to prevent the leakage of light, the flexible substrate 5 may be an opaque substrate, and the flexible substrate 5 may function also as the light shielding member.

In this manner, also in a case where the light-shielding member is a light absorbing member, similarly to the case where the light shielding member is a reflecting member, it is possible to prevent light leaking out from the rear surface side of the flexible substrate 5. Accordingly, it is possible to prevent the leakage of light to am outside during treatment, thus making it possible to reduce a burden of eyes of a patient or a surrounding person such as his/her family. In addition, since it is unnecessary to consider a surrounding person as to the leakage of light, it is also possible to reduce a mental burden of the patient or his/her family.

(Spacer 32)

FIG. 4 is a schematic view illustrating an application example in treatment with the light irradiation substrate 1 according to the present embodiment.

For the treatment using the light irradiation substrate 1, the LED chips 4 are opposed to an affected part 33 and the external connection unit 12 is connected to the external power source to thereby perform light irradiation.

As illustrated in FIG. 4, in actual treatment, the spacer 32 is required in order to maintain a distance between the front surface (specifically, front surfaces of the LED chips 4) of the light irradiation substrate 1 and the affected part 33 to be constant at a time of light irradiation and fix a positional relation between the light irradiation substrate 1 and the affected part 33, particularly, a positional relation between the LED chips 4 and the affected part 33.

As the spacer 32, various forms such as one obtained by filling a plastic bag, which is processed so as to maintain a constant thickness, with water or air, an epoxy or polyurethane resin plate which is transparent and flexible, a water-absorbing polymer processed in a plate shape are able to be used.

The spacer 32 and the light irradiation substrate 1 may be integrated with each other, or may be used as different members.

The spacer 32 is able to adhere closely to the affected part 33, for example, by thinly applying white Vaseline to the affected part 33 and a periphery thereof. Similarly, for example, by thinly applying white Vaseline between the light irradiation substrate 1 and the spacer 32, it is possible to cause the light irradiation substrate 1 and the spacer 32 to adhere closely to each other.

However, for example, by bonding the spacer 32 to the front surface side of the light irradiation substrate 1 in advance, it is possible to facilitate a process of attaching the light irradiation substrate 1 to the affected part 33.

For the bond of the spacer 32 to the light irradiation substrate 1, for example, various publicly known adhesives may be used.

That is, the light irradiation substrate 1 may be a light irradiation substrate with a spacer, and may further include, for example, a not-illustrated adhesive layer and the spacer 32 on the LED protective resin domes 8 and the wiring protection film 7. In other words, the light irradiation substrate with a spacer according to the present embodiment may include the light irradiation substrate 1 according to FIG. 1 to FIG. 3, the spacer 32, and the adhesive layer that bonds the light irradiation substrate 1 and the spacer 32.

In addition, at the time of light irradiation, by mounting sensors, such as a temperature sensor and a light intensity sensor, between the spacer 32 and the affected part 33 or a skin 31 around the affected part 33, it is also possible to monitor temperature and light intensity, and to control light irradiation power by using outputs of the sensors.

Thus, the sensors such as the temperature sensor and the light intensity sensor may be mounted onto the light irradiation substrate 1 (light irradiation substrate with a spacer).

Moreover, in order to uniformize intensity of light irradiation to the affected part 33, a relation between a thickness of the spacer 32 and pitches between the centers of the LED chips 4 (that is, the pitch Px and the pitch Py) is important.

Then, when an average value of the pitches between the adjacent LED chips 4 is D and an average thickness of the spacer 32 (to be exact, a distance from the front surface of the LED chip 4 to a front surface of the spacer 32) is T, T/D preferably satisfies $T/D \geq 0.5$, more preferably satisfies $T/D \geq 0.8$. Generally, in a case where T/D is smaller than 0.5, a difference of intensity of light irradiation between a part immediately under the LED chip 4 and a part immediately under a middle part between the LED chips 4 becomes as great as about twice, so that the intensity of light irradiation becomes considerably ununiform, which is not preferable.

In the present embodiment, by covering the front surface of the flexible substrate 5 with the first electrical conducting material patterns 15 as wide as possible, it is possible to return reflection light from the affected part 33 to the affected part 33 and uniformize the intensity of light irradiation to the affected part 33. However, as described above, since there is a tendency that, when T/D is small, the difference of the intensity of light irradiation between the part immediately under the LED chip 4 and the part immediately under the middle part between the LED chips 4 becomes large, it is desired that T/D is not less than 0.5.

Note that, in the present embodiment, for example, a resin plate obtained by molding "CEP-10A" (trade name, manufactured by NISSIN RESIN Co., Ltd.) which is epoxy transparent low-viscosity resin into a square of about 30 mm having a thickness of about 7 mm is used as the spacer 32, and T/D is set to be 7 mm/5 mm=1.4, as described in an exemplary embodiment below.

Note that, in terms of uniformity of the intensity of light irradiation, there is no particular upper limit for a value of T/D. However, as to facility of use at a time of actual treatment, handleability is improved as the spacer 32 is thinner. Thus, in terms of handleability, it is desired that the thickness of the spacer 32 is set so that T/D becomes, for example, 2.0 or less.

Moreover, in terms of waste of energy in a case where an end of the flexible substrate 5 protrudes to an outside more than the spacer 32, or prevention of light irradiation to a normal part, it is desired that the spacer 32 is formed so as to have the same size as the light irradiation substrate 1 or so as to be larger than the light irradiation substrate 1. However, even in a case where the spacer 32 is smaller than the light irradiation 1, compared with current phototherapy that an affected part is irradiated with light all at once by a large lamp, a loss is far less.

Exemplary Embodiment 1

In the present exemplary embodiment, in order to verify an effect of the light irradiation substrate 1, as illustrated in FIG. 4, an ulcer formed on a back of a mouse 30 was caused to be infected with "MRSA", and the light irradiation substrate 1 of the present embodiment was applied to phototherapy using systemic administration of "ALA" and, as therapeutic light, blue-violet light 34 whose wavelength is 410 nm. A part of "ALA" is converted into "PpIX" in a body of "MRSA". "PpIX" is a photosensitizing material, and, as described in NPL 1, it is considered that "PpIX" is decomposed by the blue-violet light 34, active oxygen which is generated during the decomposition attacks "MRSA", and "MRSA" is thereby able to be reduced, so that the phototherapy is expected as a safe therapeutic method for a bacteria having antibiotic resistance.

In the present exemplary embodiment, as the affected part 33, an ulcer in a round shape whose diameter was about 20 mm was formed on the skin 31 of the back of each of two mice 30 used for an experiment, and the affected part 33 was infected with "MRSA". "ALA" was administered to one mouse 30 in advance, and light irradiation was performed. Nothing was done for the other mouse 30. In this state, a change in a size of the ulcer of each mouse 30 is observed.

For the light irradiation, the light irradiation substrate 1 in which 16 blue-violet LEDs, as the LED chips 4, were mounted on the flexible substrate 5 which was a square of 30 mm and the 16 LED chips 4 were connected in series by the wirings 2 was used as illustrated in FIG. 2 and FIG. 3. The light irradiation substrate 1 was connected to an external constant current power source, which was capable of raising a voltage to 55 V, via the external connection unit 12. Each distance D between the centers of the LED chips 4 was set to be about 5 mm.

As described above, the resin plate obtained by molding "CEP-10 A" which was epoxy transparent low-viscosity resin into a square of about 30 mm having a thickness of about 7 mm was used as the spacer 32. After placing the spacer 32 on the affected part 33, the light irradiation substrate 1 was caused to closely adhere onto the spacer 32 so that the LED chips 4 face the affected part 33. White Vaseline is thinly applied to the affected part 33 and the periphery thereof in order to cause the spacer 32 and the affected part 33 to closely adhere. A similar processing is performed also between the light irradiation substrate 1 and the spacer 32.

Next, an electrical current of 100 mA was supplied to the light irradiation substrate 1 from the constant current power source via the external connection unit 12 for 8 minutes, and intensity of light irradiation was measured. Note that, although an output is slightly reduced over time, since average irradiation intensity was about 104 mW/cm$^2$, supplying time (light irradiation time) was decided as 8 minutes for achieving a target dose of about 50 J/cm$^2$.

When the sizes of the ulcers of the two mice 30 after the light irradiation are observed, the ulcer which was not subjected to light irradiation was not reduced even after one week has passed. On the other hand, the ulcer of the mouse 30 for which light irradiation was performed was apparently reduced every day. Since the ulcer was reduced as a whole, it is possible to presume an effect that "MRSA" is almost uniformly killed in the whole surface of the affected part 33. Thus, it has been proved that, by using the light irradiation substrate 1, it is possible to almost uniformly perform light irradiation even to the affected part 33 which has a curved surface and which is not flat and is relatively small as the back of the mouse 30 illustrated in FIG. 4.

Similar measurement was performed by using a light irradiation substrate having the same configuration as that of the light irradiation substrate 1 except that the dummy pattern 6 was not included. As a result, the intensity of light irradiation was 83 mW/cm$^2$, and supplying time (light irradiation time) of 10 minutes was required for achieving the target dose of about 50 J/cm$^2$. Thus, it has been proved that the intensity of light irradiation is improved by 20% by providing the dummy pattern 6 in the light irradiation substrate 1, that is, by covering the front surface of the flexible substrate 5 with the first electrical conducting material patterns 15 with high coverage.

As above, the light irradiation substrate 1 according to the present embodiment is suitable for treatment for a relatively small diseased part, and is able to realize almost uniform and efficient light irradiation even for an affected part that is not flat without forcing a patient to take an unnatural posture as an irradiation device of a lamp type. Moreover, since it is possible to improve intensity of irradiation light as described above, treatment time is able to be shortened. Accordingly, it is possible to suppress a side effect due to light irradiation to a minimum and suppress a physical burden, a mental burden, an economic burden, and the like of a patient and his/her family.

Although description below will be given on the assumption of pattern arrangement using the dummy pattern 6, the above-described effect is able to be similarly realized also in a case where the high coverage of the first electrical conducting material patterns 15 is realized only by the wiring patterns described in Embodiment 1.

Embodiment 2

Another embodiment of the invention will be described as follows on the basis of FIG. 7. Note that, in the present embodiment, description will be given for a different point from Embodiment 1, the same reference signs are assigned to constituents having the same functions as those of the constituents described in Embodiment 1, and description thereof is omitted.

(Schematic Configuration of Light Irradiation Substrate 1)

Figure 7:
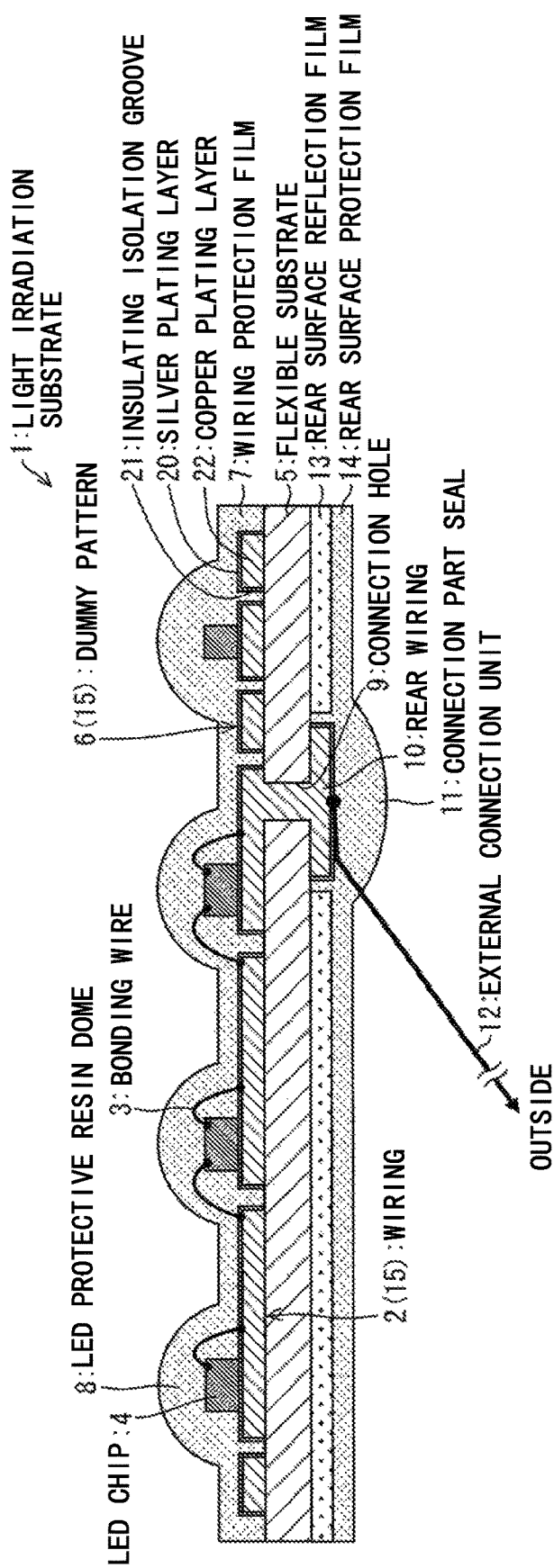
FIG. 7 is a schematic sectional view illustrating a configuration of a light irradiation substrate according to Embodiment 2 of the invention.

FIG. 7 is a schematic sectional view illustrating a configuration of the light irradiation substrate 1 according to the present embodiment.

The light irradiation substrate 1 according to the present embodiment is the same as the light irradiation substrate 1 according to Embodiment 1 except for a following point.

In the present embodiment, the flexible substrate 5 is formed of resin (for example, polycarbonate) which has translucency with respect to light emitted by the LED chip 4.

Although a configuration of the front surface side of the flexible substrate 5 is the same as that of Embodiment 1, as a rear surface reflection film 13, an aluminum thin film which is highly reflecting metal (high reflectance material) is arranged in an area as wide as possible in the rear surface side of the flexible substrate 5 as illustrated in FIG. 7. The rear surface reflection film 13 is covered with a rear surface protection film 14 for preventing corrosion.

As described in Embodiment 1, the insulating isolation groove 21 is provided between the first electrical conducting material patterns 15 as a gap. Thus, light slightly leaks out to the rear surface side of the flexible substrate 5 through the gap between the first electrical conducting material patterns 15.

Then, in the present embodiment, by forming the rear surface reflection film 13 on the rear surface of the flexible substrate 5 as described above, light (specifically, light reflected from an affected part side) leaking out from the gap to the rear surface side of the flexible substrate 5 is reflected by the rear surface reflection film 13 to be returned to the affected part side.

Note that, in the present embodiment, although the aluminum thin film is arranged as the rear surface reflection film 13 in an area as wide as possible in the rear surface side of the flexible substrate 5 as described above, the rear surface reflection film 13 is required only to be formed at least in a part of the rear surface of the flexible substrate 5, which faces the gap.

Note that, a thickness of the rear surface reflection film 13 is not limited particularly, and may be appropriately set in accordance with a type of the rear surface reflection film 13 so that the light irradiation substrate 1 is flexible as a whole and light leaking out from the gap to the rear surface side of the flexible substrate 5 is able to be returned to the affected part side.

In a case where the rear surface reflection film 13 is an aluminum film, the thickness of the rear surface reflection film 13 may be set within a range of 50 nm to 50 µm, for example.

Exemplary Embodiment 2

In the present exemplary embodiment, in order to verify an effect of the light irradiation substrate 1, an experiment similar to that of the exemplary embodiment 1 was performed, except that the light irradiation substrate 1 illustrated in FIG. 7 was used instead of the light irradiation substrate 1 according to Embodiment 1.

As a result, by using both of the dummy pattern 6 and the rear surface reflection film 13 configured by an aluminum thin film whose thickness was 1 µm as patterns for reflection other than the wirings 2 as illustrated in FIG. 7, compared with a case where only the dummy pattern 6 is used as a pattern for reflection other than the wirings 2, intensity of light irradiation was improved by 3%, and light irradiation time for achieving the target dose of about 50 J/cm$^2$ was shortened by 3%.

Note that, in the present embodiment, since the dummy pattern 6 is formed on the front surface side of the flexible substrate 5, only light leaking out from the insulating isolation groove 21 to the rear surface side of the flexible substrate 5 is reflected, so that improvement of an effect of preventing a loss of light as described above is not so great. However, by providing the rear surface reflection film 13 as described above, no light leaks out to the rear surface side of the flexible substrate 5, so that it is unnecessary to consider a surrounding person as to the leakage of light.

Moreover, a similar experiment was performed by using only the aluminum thin film as the pattern for reflection other than the wirings 2 instead of the dummy pattern 6. As a result, compared with the case where only the dummy pattern 6 is used as the pattern for reflection other than the wirings 2, intensity of light irradiation was improved by 13.5% and light irradiation time was shortened by 13.5%.

From the results above, it is found that, even when the rear surface reflection film 13 is used instead of dummy pattern 6, it is possible to improve intensity of irradiation light and shorten treatment time, but, compared with the case where only the rear surface reflection film 13 is used, it is possible to substantially improve intensity of light irradiation by using the dummy pattern 6 as described in the exemplary embodiment 1. In addition, it is found that it is possible to further improve intensity of light irradiation by using both of the dummy pattern 6 and the rear surface reflection film 13.

Exemplary Embodiment 3

Although the aluminum thin film was used for the rear surface reflection film 13 in the exemplary embodiment 2, when an aluminum film, which is thick is used, as the rear surface reflection film 13, it is possible to expect an effect of diffusing heat of the LED chips 4 to a periphery thereof to suppress an increase in temperature of the LED chips 4.

Then, in the present exemplary embodiment, an aluminum film whose thickness was 30 µm was used as the rear surface reflection film 13 instead of the aluminum thin film in the exemplary embodiment 2.

In a case where such a thick aluminum film is arranged as the rear surface reflection film 13, an effect of lowering temperature of the LED chips 4 is achieved by a heat diffusion effect.

As a result, compared with a case where the aluminum film is not arranged on the rear surface of the flexible substrate 5, the temperature of the LED chips 4 was reduced to 50° C. from 60° C. and light intensity was improved by about 2%.

Note that, as illustrated in the exemplary embodiment 2, the effect of improving irradiation intensity by reflection of the aluminum film is 3%. Accordingly, by arranging such a thick aluminum, film as the rear surface reflection film 13, light intensity (light-emitting efficiency) is improved by 5% in total, and, as a result, shortening light irradiation time from 8 minutes to 7 minutes and 36 seconds, that is, by 24 seconds is achieved.

Embodiment 3

Still another embodiment of the invention will be described as follows on the basis of FIG. 8 to FIG. 10. Note that, in the present embodiment, description will be given for a different point from Embodiments 1 and 2, the same reference signs are assigned to constituents having the same functions as those of the constituents described in Embodiment 1, and description thereof is omitted.

(Schematic Configuration of Light Irradiation Substrate 1)

Figure 8:
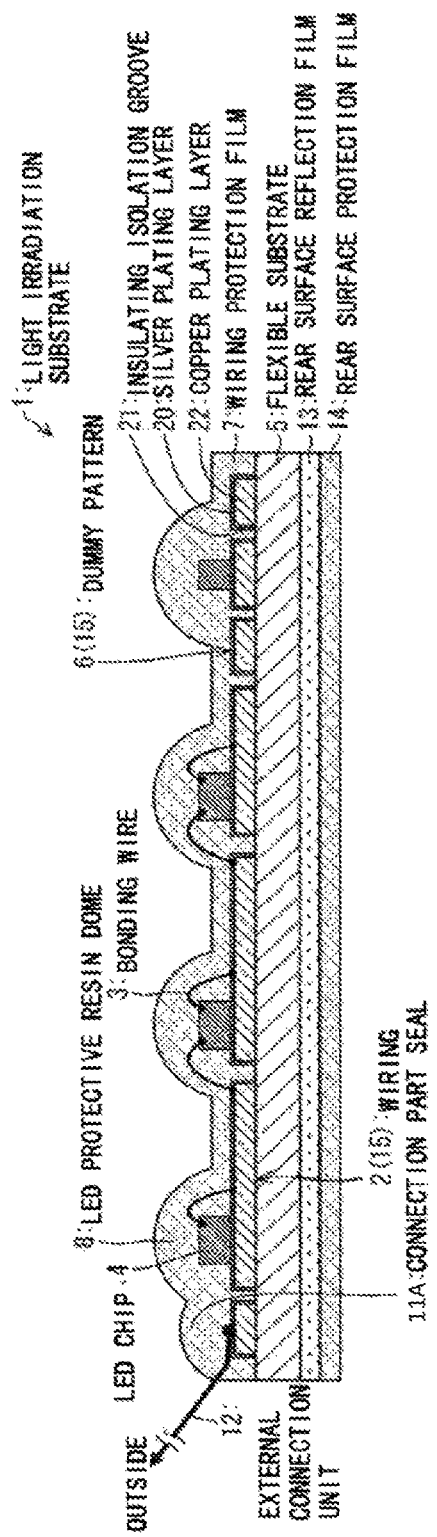
FIG. 8 is a schematic sectional view illustrating a configuration of a light irradiation substrate according to Embodiment 3 of the invention.

FIG. 8 is a schematic sectional view illustrating a configuration of the light irradiation substrate 1 according to the present embodiment. FIG. 9 is a schematic front surface view illustrating the configuration of the light irradiation substrate 1 according to the present embodiment.

Figure 9:
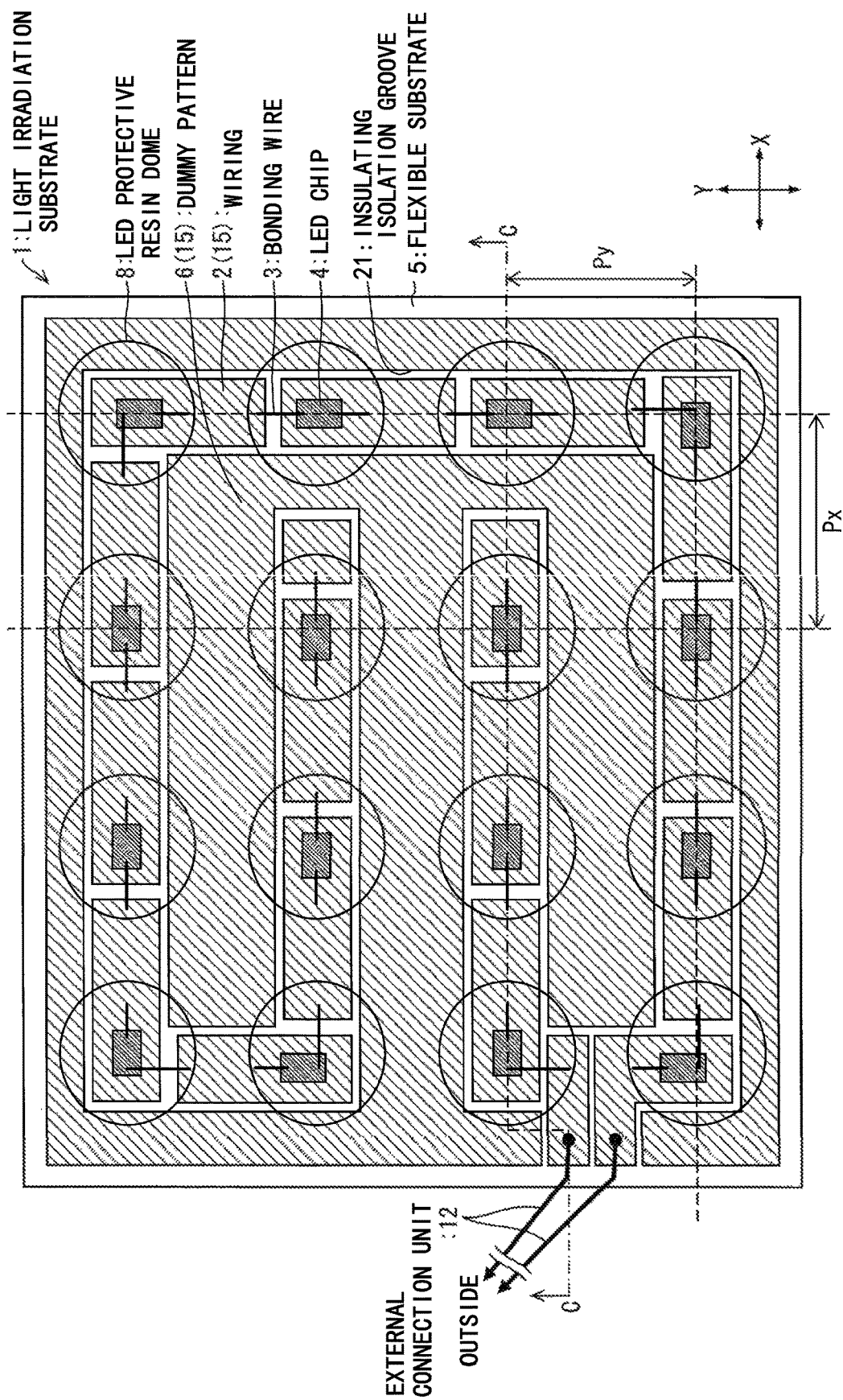
FIG. 9 is a schematic front surface view illustrating the configuration of the light irradiation substrate according to Embodiment 3 of the invention.

FIG. 8 corresponds to a sectional view taken along a C-C line of the light irradiation substrate 1, which is illustrated in FIG. 9. Note that, for convenience of illustration, illustration of the wiring protection film 7 is omitted in FIG. 9.

The light irradiation substrate 1 according to the present embodiment is different in an installation place of the external connection unit 12 from the light irradiation substrate 1 according to Embodiments 1 and 2. Description will be given below for the light irradiation substrate 1 according to the present embodiment by comparing with that of Embodiment 2.

The light irradiation substrate 1 according to the present embodiment is the same as the light irradiation substrate 1 according to Embodiment 2, except for the following point.

In the present embodiment, as illustrated in FIG. 8 and FIG. 9, a substrate size of the flexible substrate 5 is set to be 30 mm×33 mm, and the external connection unit 12 is connected to a part of the wirings 2 on the front surface side in one end in a longitudinal direction of the flexible substrate 5. Accordingly, in a wire connection part of the wirings 2 and the external connection unit 12 on the front surface side, the connection part seal 11A that covers the wire connection part is provided in the present embodiment.

Note that, in the present embodiment, a wiring material, arrangement and a connecting method of the LED chips 4, the wiring protection film 7, the LED protective resin domes 8, the connection part seal 11A, the rear surface reflection film 13, the rear surface protection film 14, and the like are the same as those of Embodiment 1 and Embodiment 2.

In the present embodiment, connecting work (soldering) of the external connection unit 12 is required on the formation surface of the LED chips 4 and the wirings 2 after mounting the LED chips 4. Accordingly, there is a possibility that the yield of production of the light irradiation substrate 1 is lowered due to reduction in reflectance, which is caused by a stain on the front surface of any of the wirings 2 and the dummy pattern 6, short circuit which is caused when dust mounts on the insulating isolation groove 21, or the like.

However, according to the present embodiment, it is not necessary to provide the rear wirings 10, with which the external connection unit 12 is connected, on the rear surface side of the flexible substrate 5. Thus, no connection hole 9 is required.

Moreover, since there is no necessity to provide the rear wirings 10 on the rear surface side of the flexible substrate 5 in the present embodiment, in a case where the rear surface reflection film 13 is provided on the rear surface side of the flexible substrate 5 as illustrated in FIG. 8, it is possible to provide the rear surface reflection film 13 so as to cover the entirety of the insulating isolation groove 21 in a plan view.

Furthermore, in the case where the rear surface reflection film 13 is provided on the rear surface side of the flexible substrate 5 as illustrated in FIG. 8, it is possible to provide the rear surface reflection film 13 which is flat on the whole of the rear surface of the flexible substrate 5, for example.

As described above, by connecting the external connection unit 12 to a part of the wirings 2 on the front surface side of the flexible substrate 5, it is possible to simplify the configuration compared with the case where the external connection unit 12 is connected to the rear surface side of the flexible substrate 5. Thus, it is possible to simplify a manufacturing process, so that costs are able to be reduced.

Note that, as a countermeasure against reduction in the production yield, it is also considered to install the external connection unit 12 after forming the wiring protection film 7 and the LED protective resin domes 8. In this case, however, it is necessary to form the connection part seal 11A separately, resulting in disadvantage in terms of costs.

Figure 10:
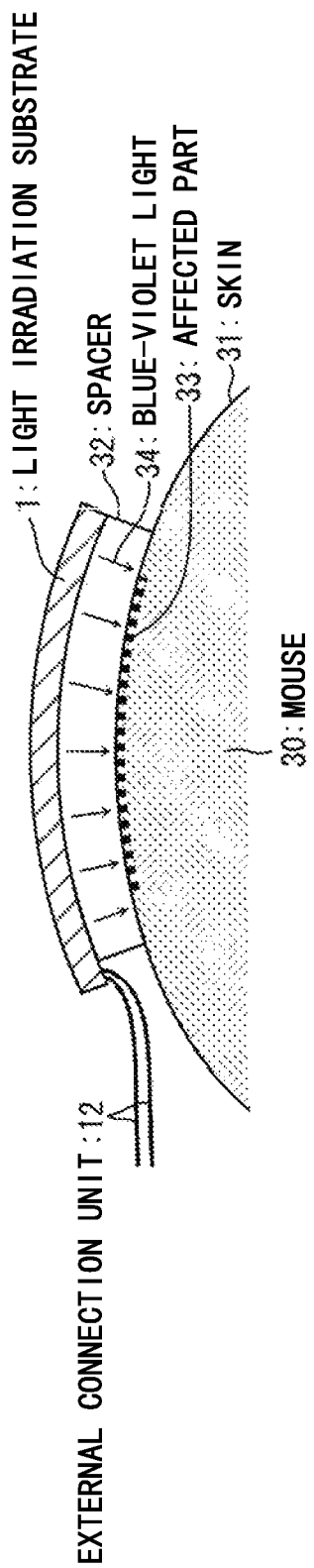
FIG. 10 is a schematic view illustrating an application example in treatment with the light irradiation substrate according to Embodiment 3 of the invention.

FIG. 10 is a schematic view illustrating an application example in treatment with the light irradiation substrate 1 according to the present embodiment.

Consideration is given so that the spacer 32 does not overlap with the external connection unit 12 when applying the light irradiation substrate 1 to actual treatment. Specifically, as illustrated in FIG. 10, the spacer 32 which is smaller than the light irradiation substrate 1 is used, and the spacer 32 is arranged so as to avoid an installation part of the external connection unit 12.

Exemplary Embodiment 4

In the present exemplary embodiment, in order to verify an effect of the light irradiation substrate 1, an experiment similar to that of the exemplary embodiment 3 was performed, except that the light irradiation substrate 1 illustrated in FIG. 8 and FIG. 9 was used instead of the light irradiation substrate 1 according to Embodiment 2.

According to the present exemplary embodiment, intensity of light irradiation was nearly the same as that of the exemplary embodiment 3, and light irradiation time was 7 minutes and 36 seconds, so that the same effect as that of the exemplary embodiment 3 is able to be achieved.

Embodiment 4

Still another embodiment of the invention will be described as follows on the basis of FIG. 11. Note that, in the present embodiment, description will be given for a different point from Embodiments 1 to 3, the same reference signs are assigned to constituents having the same functions as those of the constituents described in Embodiments 1 to 3, and description thereof is omitted.

(Schematic Configuration of Light Irradiation Substrate 1)

Figure 11:
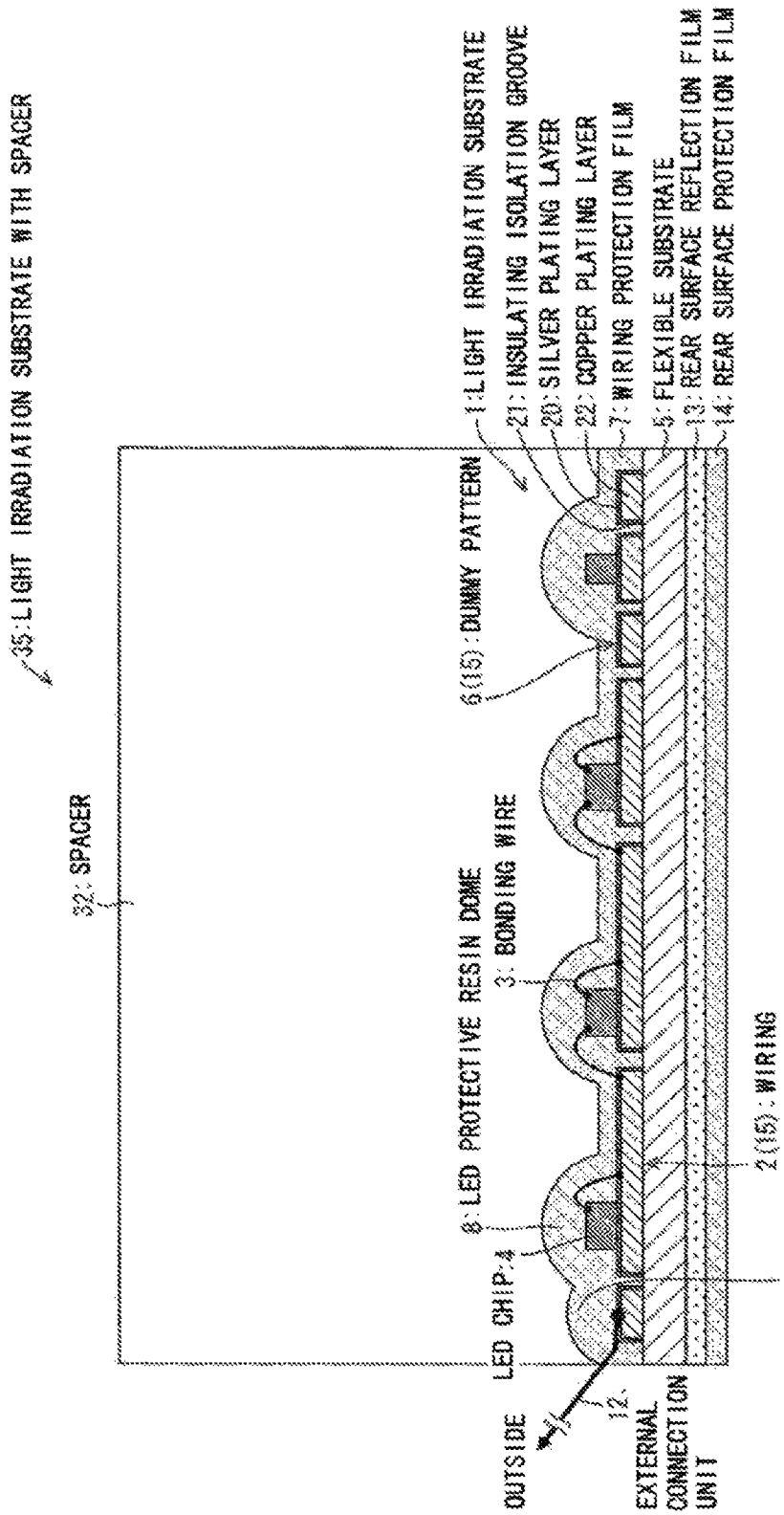
FIG. 11 is a schematic sectional view illustrating a configuration of a light irradiation substrate with a spacer according to Embodiment 4 of the invention.

FIG. 11 is a schematic sectional view illustrating a configuration of a light irradiation substrate with a spacer 35 according to the present embodiment.

The light irradiation substrate with a spacer 35 according to the present embodiment is different from the light irradiation substrate 1 according to Embodiments 1 to 3 in that the spacer 32 is connected onto the light irradiation substrate 1. Description will be given below for the light irradiation substrate with a spacer 35 according to the present embodiment by comparing with that of Embodiment 3.

The light irradiation substrate with a spacer 35 according to the present embodiment includes the light irradiation substrate 1 and the spacer 32 that is formed integrally with the light irradiation substrate 1. Note that, the light irradiation substrate 1 illustrated in FIG. 11 is the same as the light irradiation substrate 1 illustrated in FIG. 8 and FIG. 9. Moreover, a material of the spacer 32 is not particularly limited, as long as the material transmits light emitted by the LED chips 4 and is flexible. The material of the spacer 32 may be the same as or different from those of the wring protection film 7 and the LED protective resin domes 8, and, when insulating resin is used for each of the wiring protection film 7, the LED protective resin domes 8, and the spacer 32, it is possible to obtain the light irradiation substrate with a spacer 35 in which the spacer 32 and the light irradiation substrate 1 serving as a light-emitting substrate are integrated.

(Manufacturing Method of Light Irradiation Substrate with Spacer 35)

An example of a manufacturing method of the light irradiation substrate with a spacer 35 according to the present embodiment will be described below.

In the present embodiment, after the light irradiation substrate 1 described in Embodiment 3 is formed, the light irradiation substrate 1 is arranged in a bottom of a not-illustrated mold.

Next, a resin layer whose thickness is about 7 mm is formed as the spacer 32 by pouring "CEP-10 ft." which is epoxy transparent low-viscosity resin into the mold and polymerizing the resultant while raising temperature thereof to 40° C., 60° C., 80° C., and 110° C. Thereby, the light irradiation substrate with a spacer 35 in which the spacer 32 and the light irradiation substrate 1 serving as the light-emitting substrate are integrated is able to be formed.

Note that, in the present embodiment, the epoxy resin for the spacer 32 is formed after forming the wiring protection film 7, the LED protective resin domes 8, and the connection part seal 11A, as described above. However, when the process is optimized, it is also possible to form the resin for the spacer 32 by omitting a part of the wiring protection film 7, the LED protective resin domes 8, and the connection part seal 11A, and cause the spacer 32 to function as a protection film for the wirings 2 and the LED chips 4.

Exemplary Embodiment 5

In the present exemplary embodiment, in order to verify an effect of the light irradiation substrate with a spacer 35, an experiment similar to that of the exemplary embodiment 3 was performed similarly to the exemplary embodiment 3, except for the following condition.

In the present exemplary embodiment, the light irradiation substrate with a spacer 35 which has been manufactured in the aforementioned manufacturing method and had a thickness of 7.1 mm and a size of 30 mm×33 mm was placed on the affected part 33 which has been infected with "MRSA" in a similar manner to the exemplary embodiment 1, and slowly deformed so as to fit the affected part 33 by lightly applying a force. Note that, in order to make the spacer 32 and the affected part 33 closely adhere to each other, white Vaseline was thinly applied to the affected part 33 and the periphery thereof.

According to the present exemplary embodiment, intensity of light irradiation is nearly the same as that of the exemplary embodiment 3, and light irradiation time was 7 minutes and 36 seconds, so that the same effect as that of the exemplary embodiment 3 was able to be achieved.

Embodiment 5

Still another embodiment of the invention will be described as follows on the basis of FIG. 12. Note that, in the present embodiment, description will be given for a different point from Embodiments 1 to 4, the same reference signs are assigned to constituents having the same functions as those of the constituents described in Embodiments 1 to 4, and description thereof is omitted.

(Schematic Configuration of Light Irradiation Substrate 1)

Figure 12:
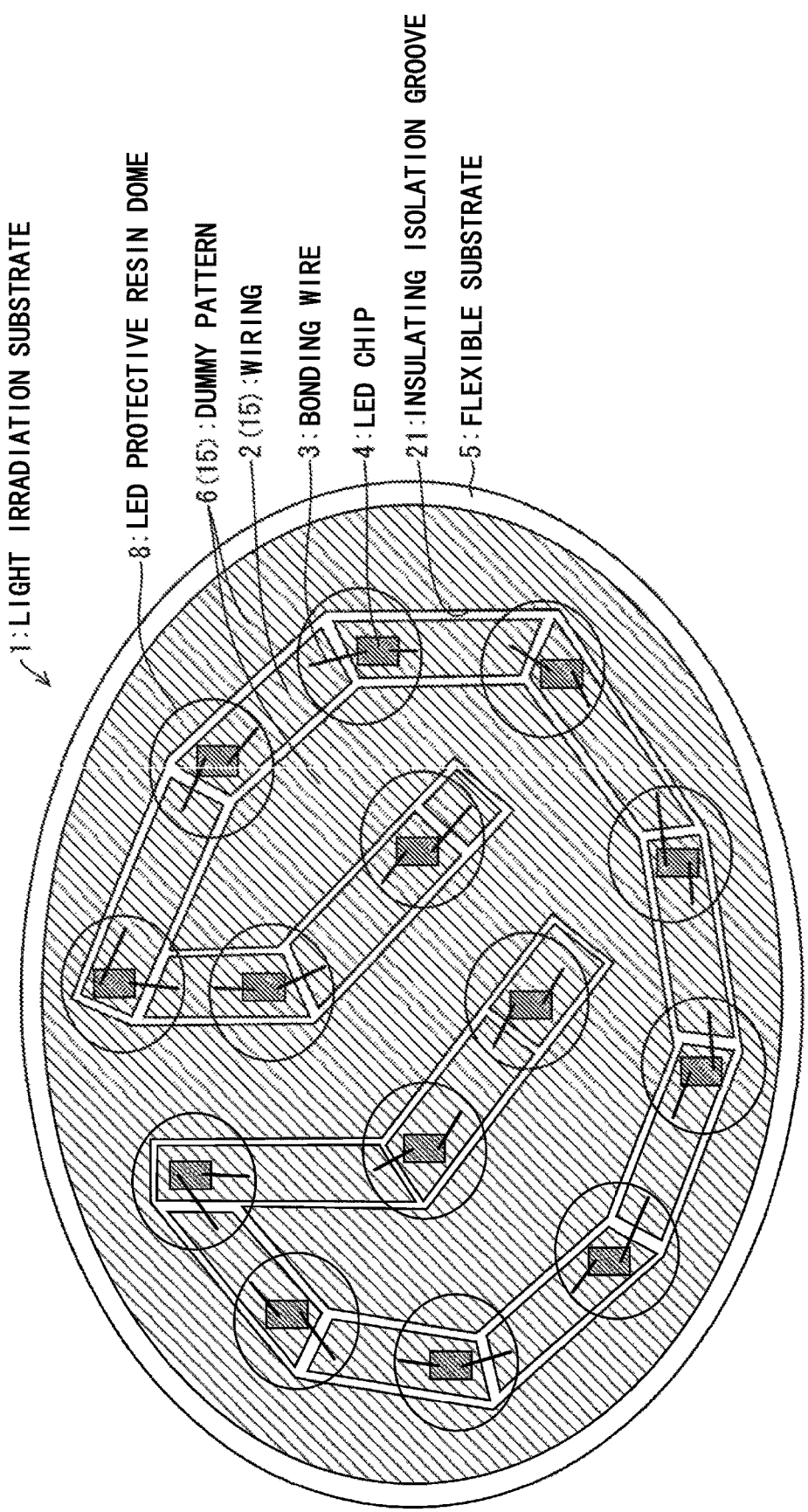
FIG. 12 is a schematic plan view illustrating a configuration of a light irradiation substrate according to Embodiment 5 of the invention.

FIG. 12 is a schematic plan view illustrating a configuration of the light irradiation substrate 1 according to the present embodiment.

The present embodiment is different from Embodiments 1 to 4 in that a substrate shape of the flexible substrate 5 is changed to an elliptical shape. The substrate shape of the flexible substrate 5 may be a round shape or another polygonal shape such as a hexagonal shape or an octagonal shape, and various shapes are possible in accordance with convenience.

The light irradiation substrate 1 as in the present embodiment is suitable for treatment for an affected part whose area is extremely small.

Compared with the exemplary embodiment 3, the different-point of the light irradiation substrate 1 according to the present embodiment will be hereinafter described by taking, as an example, a case where the flexible substrate 5 in the elliptical shape is used.

Exemplary Embodiment 6

In the present exemplary embodiment, in order to verify an effect of the light irradiation substrate with a spacer 35, an experiment similar to that of the exemplary embodiment 3 was performed similarly to the exemplary embodiment 3, except for the following condition.

Note that, in the present exemplary embodiment, the affected part 33 whose diameter was about 10 mm was targeted.

As illustrated in FIG. 12, in the present exemplary embodiment, the flexible substrate 5 whose minor axis was 22 mm and whose major axis was 26 mm and on which 14 blue-violet LEDs were mounted as the LED chips 4 was formed. The wirings 2 were provided so as to connect all of the 14 LED chips 4 in series, and the wirings 2 were set to allow connection to a constant current power source capable of raising a voltage up to 55 V.

An average pitch between the LED chips 4 was about 4.5 mm. In a case where the flexible substrate 5 is in a shape other than a rectangular (a square or a rectangle), when the LED chips 4 are arranged along an external form of the flexible substrate 5, the LED chips 4 are not disposed in a two-dimensional regular array. In the present exemplary embodiment, pitches between the LED chips 4 include variations of about ±1 from 4.5 mm.

In the present exemplary embodiment, rectangular elements whose sizes were 320 μm×800 μm were used for the LED chips 4, and were arranged so that long sides of the LED chips 4 were perpendicular to a direction of the major axis of the elliptical flexible substrate 5. Thereby, it was possible to improve uniformity of light intensity.

Similarly to the exemplary embodiment 3, a resin plate obtained by molding "CEP-10A" which was epoxy transparent low-viscosity resin into a square of about 30 mm whose thickness was about 7 mm was used for the spacer 32 (not illustrated). Moreover, also in the present exemplary embodiment, similarly to the exemplary embodiment 3, after placing the spacer 32 on the affected part 33, the light irradiation substrate 1 was made to closely adhere onto the spacer 32 and the LED chips 4 were made to closely adhere to the affected part 33. Note that, similarly to the exemplary embodiment 3, in order to make the spacer 32 and the affected part 33 closely adhere to each other, white Vaseline was thinly applied to the affected part and the periphery thereof also in the present exemplary embodiment. A similar procedure was performed also between the light irradiation substrate 1 and the spacer 32.

Next, an electrical current of 100 mA was supplied to the external connection unit 12 from a not-illustrated external power source for 7 minutes and 36 seconds. Note that, when intention of light irradiation was measured with the above-described arrangement, an output was slightly reduced over time, but average irradiation intensity was about 110 mW/cm2, so that supplying time (light irradiation time) was decided as 7 minutes and 36 seconds for achieving the target dose of about 50 J/cm$^2$.

Similarly to the exemplary embodiment 3, "ALA" was administered to the mouse 30 in which a tumor whose diameter was about 10 mm was infected with "MRSA", and phototherapy was performed by the light irradiation substrate 1, and thereafter a size of an ulcer was observed. As a result, the ulcer was apparently reduced every day. Since the ulcer was reduced as a whole, it can be assumed that an effect that "MRSA" is killed almost uniformly in the entirety of the affected part 33 is achieved also in the present exemplary embodiment.

Embodiment 6

Still another embodiment of the invention will be described as follows on the basis of FIG. 13 and FIG. 14. Note that, in the present embodiment, description will be given for a different point from Embodiments 1 to 5, the same reference signs are assigned to constituents having the same functions as those of the constituents described in Embodiments 1 to 5, and description thereof is omitted.

Figure 13:
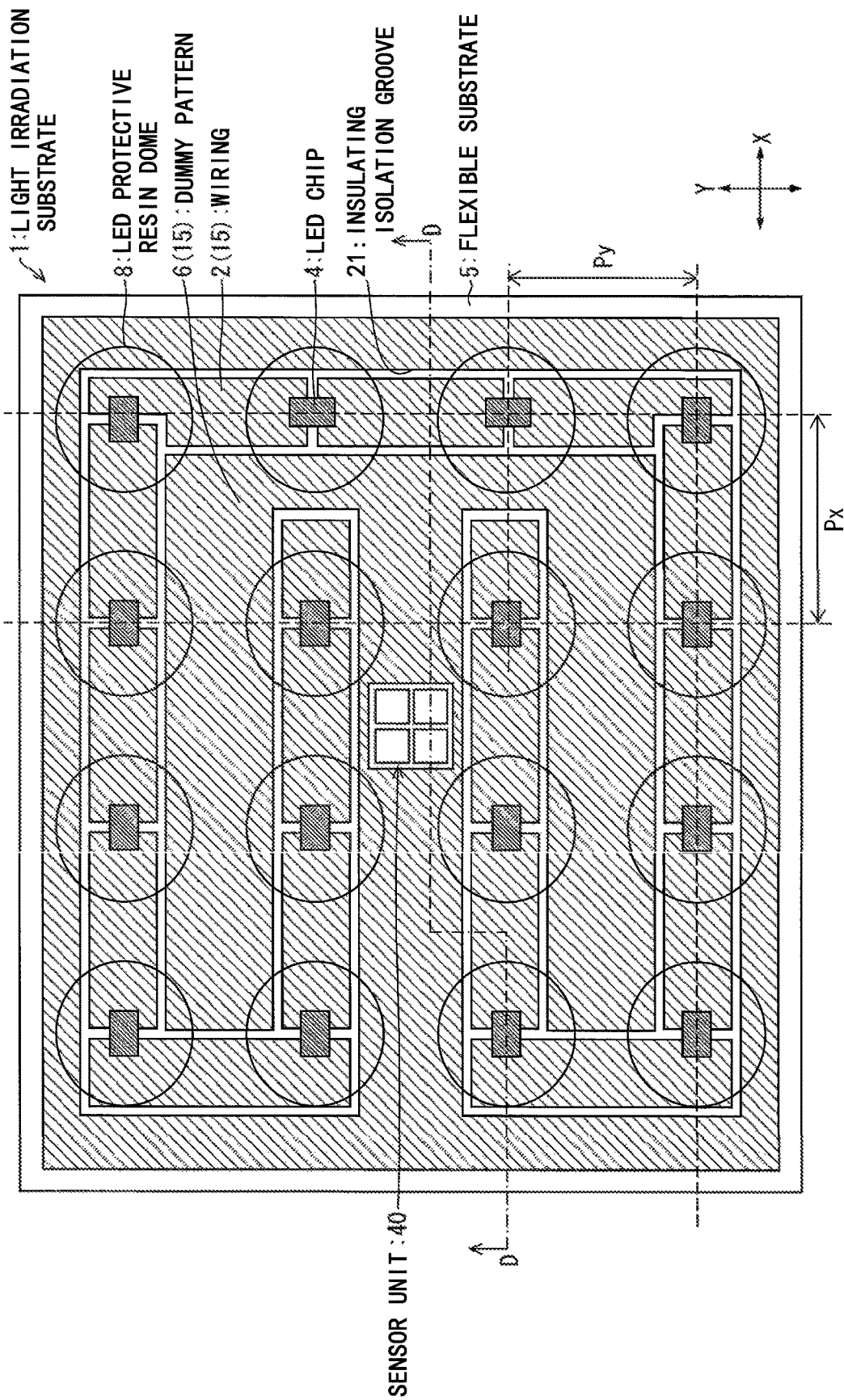
FIG. 13 is a schematic, plan view illustrating a configuration of a light irradiation substrate according to Embodiment 6 of the invention.

FIG. 13 is a schematic plan view illustrating a configuration of a light irradiation substrate according to the present embodiment. FIG. 14 is a schematic sectional view illustrating the configuration of the light irradiation substrate according to the present embodiment.

Figure 14:
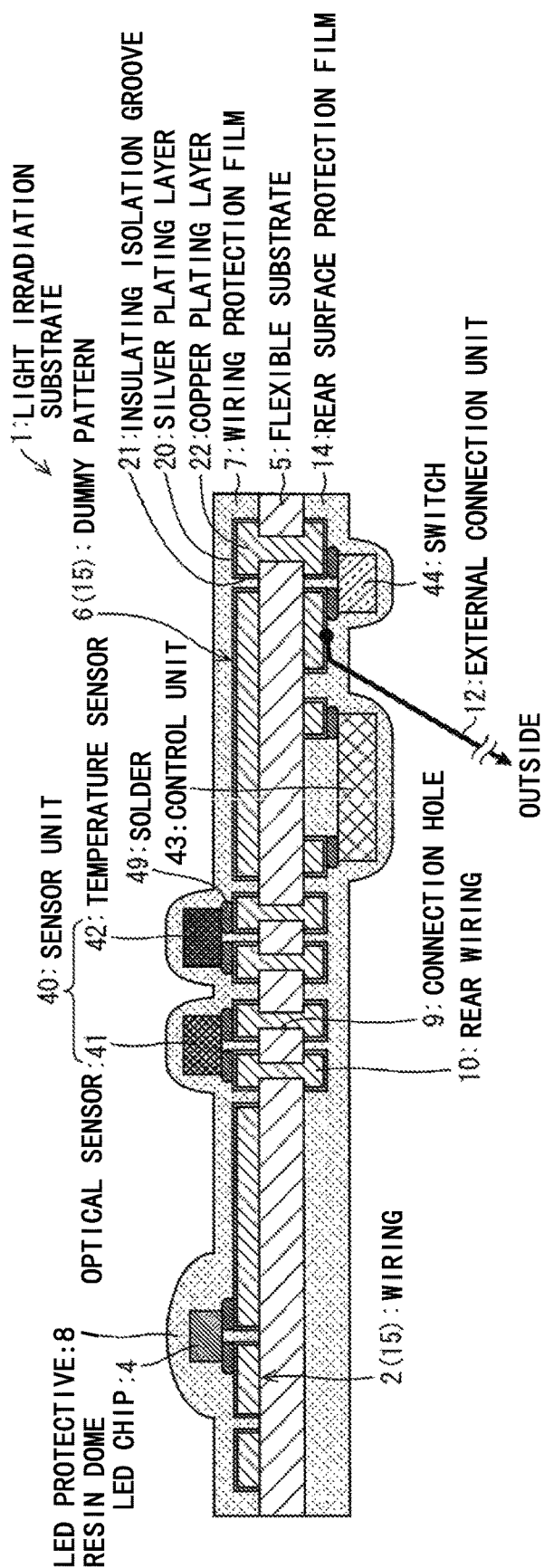
FIG. 14 is a schematic sectional view illustrating the configuration of the light irradiation substrate according to Embodiment 6 of the invention.

FIG. 14 corresponds to a sectional view taken along a D-D line of the light irradiation substrate 1, which is illustrated in FIG. 13. Note that, for convenience of illustration, illustration of the wiring protection film 7 is omitted in FIG. 13. Moreover, illustration of wirings between a sensor unit 40, a control unit 43, and a switch 44 are omitted in FIG. 13 and FIG. 14.

(Schematic Configuration of Light Irradiation Substrate 1)

The light irradiation substrate 1 according to the present embodiment has a similar configuration to the light irradiation substrate 1 according to Embodiment 1, except for the following point.

In the light irradiation substrate 1 according to the present embodiment, as illustrated in FIG. 13 and FIG. 14, the sensor unit 40, the control unit 43, and the switch 44 are mounted on the light irradiation substrate 1 as semiconductor devices for controlling light irradiation and the LED chips 4 are flip-chip mounted on the wirings 2.

The sensor unit 40 is mounted on the front surface side of the flexible substrate 5, and a front surface of the sensor unit 40 is covered with the wiring protection film 7. The control unit 43 and the switch 44 are mounted on the rear surface side of the flexible substrate 5, and front-surfaces of the control unit 43 and the switch 44 are covered with the rear surface protection film 14.

That, is, the light irradiation substrate 1 according to the present embodiment includes the flexible substrate 5, the plurality of wirings 2 which are insulated and isolated by the insulating isolation groove 21, the dummy pattern 6, the plurality of LED chips 4, the wiring protection film 7, the plurality of LED protective resin domes 8, the plurality of rear wirings 10, the external connection unit 12, the rear surface protection film 14, the sensor unit 40, the control unit 43, and the switch 44.

The different point from the light irradiation substrate 1 according to Embodiment 1 will be described in more detail below.

(Mounting Method of LED Chips 4)

Although the LED chips 4 are electrically connected to the wirings 2 with the bonding wires 3 in Embodiment 1, the LED chips 4 and the wirings 2 are connected with solder 49 as illustrated in FIG. 14 in the present embodiment.

Moreover, in the present embodiment, 16 blue-violet LED chips each having a size of 1000 μm×1000 μm are mounted on the flexible substrate 5 as the LED chips 4. The LED chips 4 are arranged in an array composed of 4 pieces×4 pieces in the X direction and Y direction, respectively, and an average pitch (Px, Py) between the LED chips 4 is set to be about 5 mm to 10 mm. In the present embodiment, so-called LED chips for flip-chip mounting in each of which a nitride semiconductor layer is grown epitaxially on a sapphire substrate and a cathode electrode and an anode electrode whose areas are almost the same are formed on a chip surface (epi-surface side) are used as the LED chips 4.

In the present embodiment, solder paste is printed on the wirings 2 as the solder 49, the LED chips 4 are mounted thereon with electrode surfaces of the LED chips 4 facing downward, and reflow is performed for connection. In addition, the semiconductor devices other than the LED chips 4 are also connected at the same time.

(Sensor Unit 40, Control Unit 43, and Switch 44)

In the present embodiment, as illustrated in FIG. 13 and FIG. 14, the sensor unit 40 including an optical sensor 41 and a temperature sensor 42 is arranged on the front side of the flexible substrate 5, so that an electrical current supplied to the LED chips 4 from the external power source via the external connection unit 12, the rear wirings 10, and the wirings 2 is able to be controlled on the basis of outputs of the optical sensor 41 and the temperature sensor 42.

As illustrated in FIG. 14, the optical sensor 41 and the temperature sensor 42 are connected to the wirings 2 with the solder 49, and separately connected to the rear-wirings 10 through the connection holes 9.

In the present embodiment, the control unit 43 (CPU) and the switch 44 (electrical current control switch) are arranged on the rear surface of the flexible substrate 5, and the light irradiation substrate 1 controls supply of power by it self.

Note that, the sensor unit 40, the control unit 43, and the switch 44 are connected with each other by not-illustrated wirings. Each of signals from the optical sensor 41 and the temperature sensor 42 is transmitted to the control unit 43.

For example, in a case where temperature detected by the temperature sensor 42 becomes higher than a predetermined level (threshold) which is set in advance, a signal for stopping the supply of power is output to the switch 44 from the control unit 43, and it is thereby possible to stop, by the switch 44, the supply of power to the LED chips 4. Moreover, in a case where an output of the optical sensor 41 does not reach or exceeds a predetermined level (threshold) which is set in advance, by operating the switch 44 in accordance with the signal from, the control unit 43, it is possible to adjust an amount of an electrical current to be supplied. Further, it is possible to stop the supply of power at a stage where accumulated, intensity of light irradiation reaches a predetermined amount (threshold).

Note that, in the present embodiment, a wiring material, arrangement and a connecting method of the LED chips 4, the wiring protection film 7, the LED protective resin domes 8, the rear surface reflection film 13, the rear surface protection film 14, and the like are the same as those of Embodiment 1 and Embodiment 2. In the present embodiment, the rear surface protection film 14 functions also as the connection part seal 11.

In a case where the sensor unit 40 is installed onto the flexible substrate 5, neither intensity of light actually received by an affected part nor temperature of the affected part is able to be measured directly. A relation between the outputs of the sensors and actual temperature and light intensity of an affected part varies also in accordance with an installation position of the sensor unit 40.

Then, in the present embodiment, the sensor unit 40 is arranged almost in the center of the substrate, correlation data regarding light intensity and temperature of an affected part is acquired in advance, and control is performed on the basis of the correlation. Thereby, it is possible to automatically control light irradiation to an affected part only by arranging the light irradiation substrate 1 onto the affected part. As a result, it is possible to save time and effort to separately install the optical sensor 41 and the temperature sensor 42 and connect outputs thereof to a power source.

Note that, when an experiment similar to that of the exemplary embodiment 1 was performed also in the present embodiment, the same effect as that of the exemplary embodiment 1 was able to be achieved also in the present embodiment.

Modified Example

Although the light irradiation substrate 1 controls supply of power by itself as described above in the present embodiment, it is also possible to control an electrical current to be supplied on a power source side by connecting a signal of the sensor unit 40 to the power source (external power source) as it is.

Moreover, although description has been given in the present embodiment by taking, as an example, a case where the sensor unit 40 includes the optical sensor 40 and the temperature sensor 42, only one of the optical sensor 41 and the temperature sensor 42 may be provided.

Embodiment 7

Still another embodiment of the invention will be described as follows on the basis of FIG. 15 to FIG. 17. Note that, in the present embodiment, description will be given for a different point from Embodiments 1 to 6, the same reference signs are assigned to constituents having the same functions as those of the constituents described in Embodiments 1 to 6, and description thereof is omitted.

Figure 15:
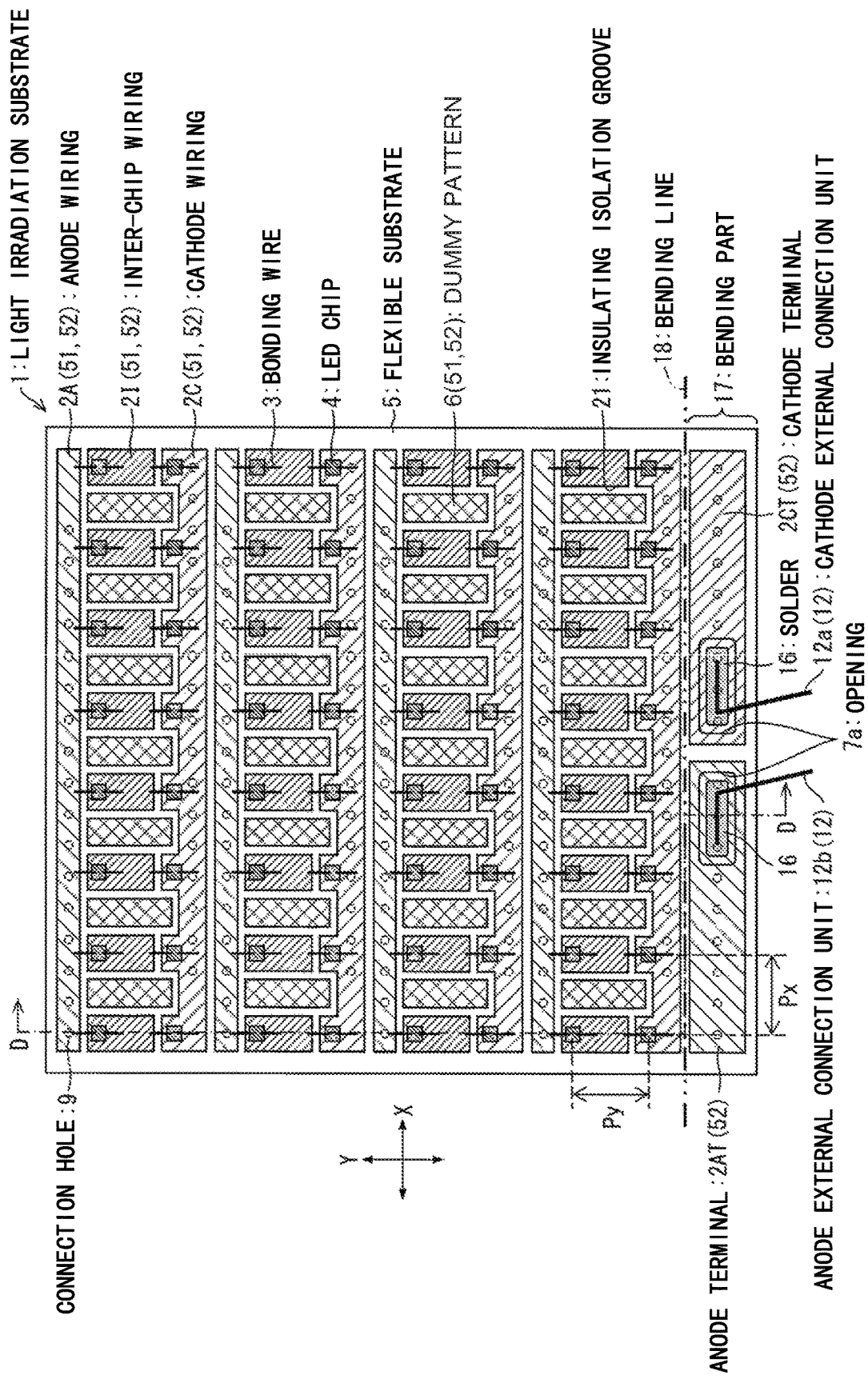
FIG. 15 is a schematic front surface view of a light irradiation substrate having a bending part according to Embodiment 7 of the invention when viewed from a front surface side in a state of being expanded on a plane.

FIG. 15 is a schematic front surface view of the light irradiation substrate 1 having a bending part 17 according to the present embodiment when viewed from, the front surface side in a state of being expanded on a plane. FIG. 16 is a schematic rear surface view of the light irradiation substrate 1 having the bending part 17 according to the present embodiment when viewed from the rear surface side in the state of being expanded on a plane.

Figure 16:
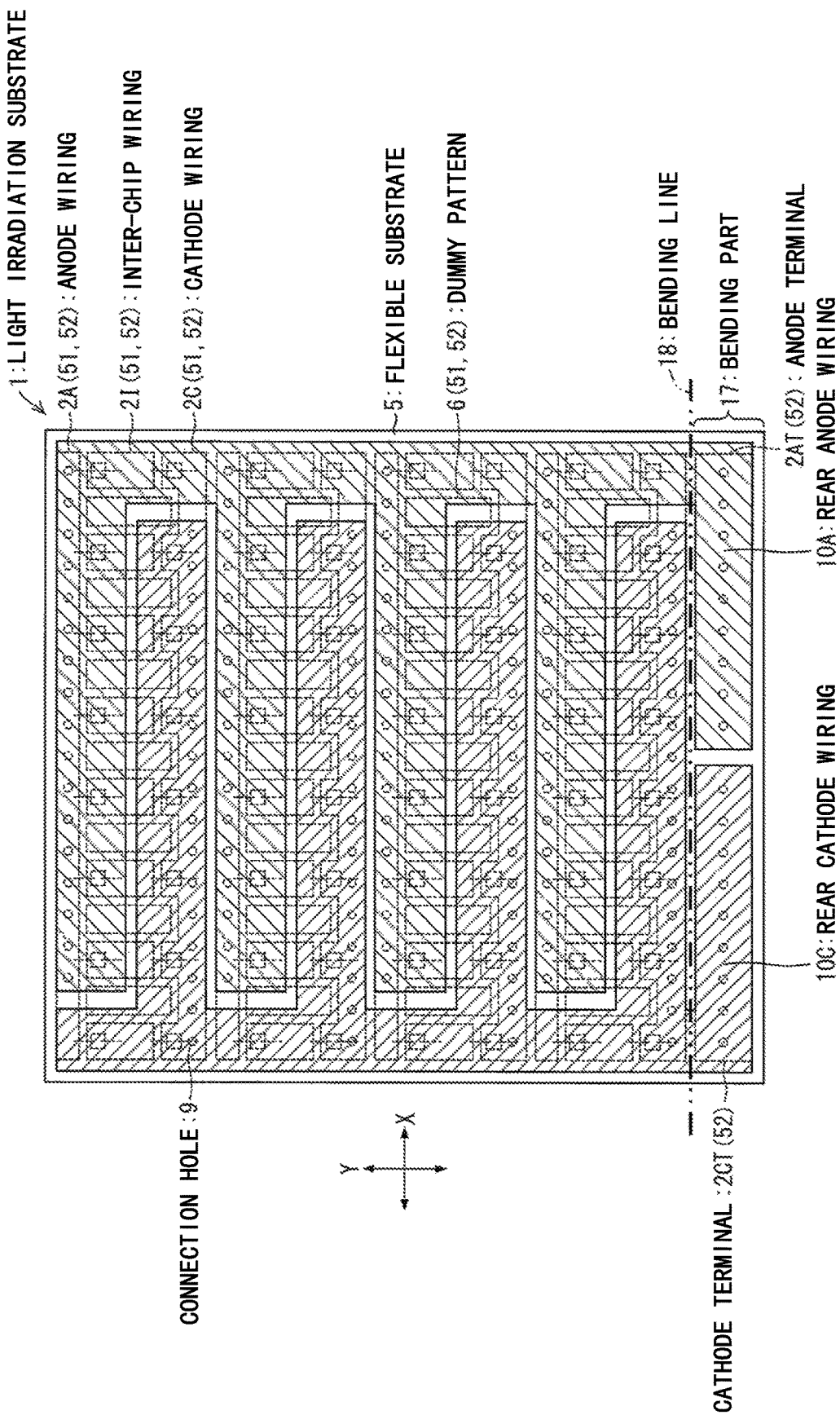
FIG. 16 is a schematic rear surface view of the light irradiation substrate having the bending part according to Embodiment 7 of the invention when viewed from a rear surface side in the state of being expanded on a plane.

That is, FIG. 15 and FIG. 16 are views which illustrate the light irradiation substrate 1 having a solid, structure in the state of being expanded on a plane, and the state where the bending part 17 of the light irradiation substrate 1 is expanded to be a plane will be hereinafter referred, to as a "developed state".

Figure 17:
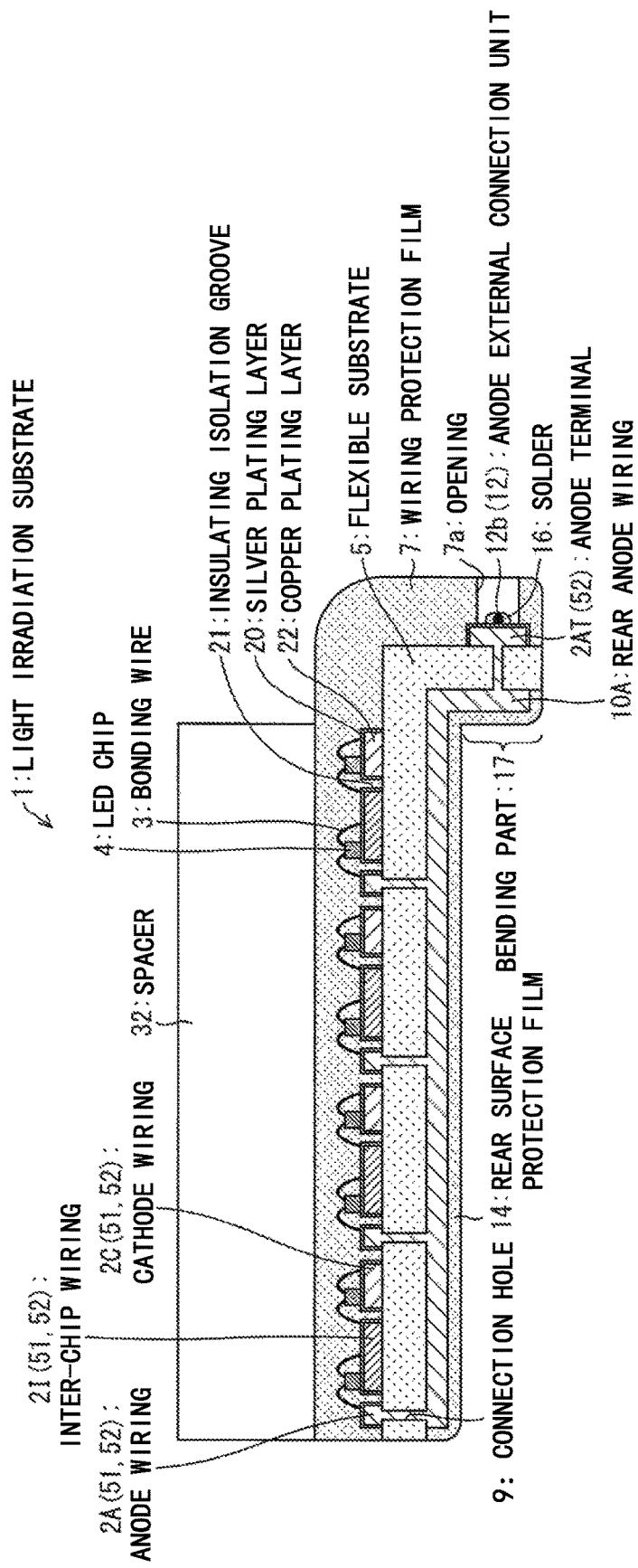
FIG. 17 is a schematic sectional view illustrating a configuration of the light irradiation substrate according to Embodiment 7 of the invention.

FIG. 17 is a schematic sectional view illustrating a configuration of the light irradiation substrate 1 according to the present embodiment. FIG. 17 corresponds to a sectional view taken along a D-D line of the light irradiation substrate 1, which is illustrated in FIG. 15. Note that, for convenience of illustration, illustration of the wiring protection film 7 and the spacer 32 which are illustrated in FIG. 17 is omitted in FIG. 15.

(Schematic Configuration of Light Irradiation Substrate 1)

The light irradiation substrate 1 according to the present embodiment is the same as the light irradiation substrate 1 according to Embodiment 1, except for the following point.

As illustrated in FIG. 15 to FIG. 17, the light irradiation substrate 1 according to the present embodiment includes the flexible substrate 5, a plurality of cathode wirings 2C (wiring patterns, first surface side wirings, second cathode wirings), a plurality of anode wirings 2A (wiring patterns, first surface side wirings, second anode wirings), a plurality of inter-chip wirings 21 (wiring patterns, first surface side wirings, inter-wiring wirings), a cathode terminal 2CT (terminal unit), an anode terminal 2AT (terminal unit), the dummy patterns 6, the plurality of LED chips 4 (light-emitting elements), the plurality of bonding wires 3, the wiring protection film 7, a rear cathode wiring 10C (wiring pattern, second surface side wiring, first cathode wiring), a rear anode wiring 10A (wiring pattern, second surface side wiring, first anode wiring), the external connection unit 12, and, as necessary, the spacer 32.

Note that, the spacer 32 may be provided integrally with the light irradiation substrate 1, or may be provided separately from the light irradiation substrate 1. That is, the light irradiation substrate 1 may be a light irradiation substrate with a spacer, or may be provided separately from the spacer 32.

On the front surface of the flexible substrate 5, the plurality of cathode wirings 2C and the plurality of anode wirings 2A are arranged in a horizontal direction. In the present embodiment, each four pieces of the cathode wirings 2C and the anode wirings 2A are arranged as illustrated in FIG. 15.

The cathode wirings 2C and the anode wirings 2A are arranged so as to extend along the X direction, and are provided alternately in the Y direction.

The inter-chip wirings 2I and the dummy patterns 6 are arranged in each space between the cathode wirings 2C and the anode wirings 2A. Each of the inter-chip wirings 2I and the dummy patterns 6 is provided so as to extend in the Y direction. In addition, the inter-chip wirings 2I and the dummy patterns 6 are arranged alternatively in the X direction.

Each of the cathode wirings 2C has a comb-like shape formed by a trunk wiring (trunk line) provided so as to extend in the X direction and a plurality of branch wirings (branch lines) each of which branches from the trunk wiring in the Y direction toward an anode wiring 2A which is adjacent to the cathode wiring 2C in the Y direction. Note that, such a shape is for clarifying mounting places of the LED chips 4 on each of the cathode wirings 2C. In a case where it is not necessary to clarify the mounting places of the LED chips 4 on each of the cathode wirings 2C, the cathode wiring 2C is not always necessary to have the comb-like shape, and may have a stick shape, for example.

Each of the inter-chip wirings 2I is provided so as to face each of the branch wirings of the cathode wiring 2C.

Each of the LED chips 4 is mounted on the branch wiring of the cathode wiring 2, and mounted on the inter-chip wiring 2I. Accordingly, two LED chips 4 are arranged side by side in the Y direction between the trunk wiring of the cathode wiring 2C and the anode wiring 2A which are adjacent in the Y direction.

Each of the inter-chip wirings 2I is electrically connected to each of the cathode wirings 2C and each of the anode wirings 2A with the bonding wires 3 connected to each of the LED chips 4. Note that, connection of the LED chips 4 will be described below.

As illustrated in FIG. 15, the cathode terminal 2CT and the anode terminal 2AT are provided side by side along one side (specifically, one short side positioned in a longitudinal direction of the flexible substrate 5) on the front side of the flexible substrate 5 in the developed state.

The cathode wirings 2C, the anode wirings 2A, the inter-chip wirings 2I, the dummy patterns 6, the cathode terminal 2CT, and the anode terminal 2AT are insulated and isolated from each other by the insulating isolation groove 21.

The cathode terminal 2CT and the anode terminal 2AT are connection parts to the external connection unit 12. Thus, the external connection unit 12 that supplies power to the light irradiation substrate 1 according to the present embodiment is arranged in the one side (that is, the aforementioned short side) on the front side of the flexible substrate 5 in the developed state as illustrated in FIG. 15.

An end of the flexible substrate 5 in the longitudinal direction, in which the external connection unit 12 is arranged, is bent by 90 degrees to the rear surface side along the aforementioned short side in order to facilitate taking out a lead wire serving as the external connection unit 12.

The external connection unit 12 incudes the cathode external connection unit 12a and the anode external connection unit 12b.

The cathode terminal 2CT is a connection part to the cathode external connection unit 12a and the anode terminal 2AT is a connection part to the anode external connection unit 12b. Thus, the cathode terminal 2CT and the anode terminal 2AT are provided in the bending part 17.

The cathode external connection unit 12a and the anode external connection unit 12b are composed of a pair of lead wires, and one end of the cathode external connection unit 12a is fixed to the cathode terminal 2CT by solder 16 that is provided on a rear surface of the cathode external connection unit 12a. Moreover, one end of the anode external connection unit 12b is fixed to the anode terminal 2AT by the solder 16 that is provided on a rear surface of the anode external connection unit 12b. The other end of each of the cathode external connection unit 12a and the anode external connection unit 12b is connected to a not-illustrated connector.

Hereinafter, for convenience of description, a position at which the flexible substrate 5 is bent along the one side (that is, the aforementioned short side) of the flexible substrate 5 is referred to as a "bending line 18", and indicated with a two-dot chain line in FIG. 15 and FIG. 16. Moreover, a part in the end side of the flexible substrate 5, which is bent along the bending line 18, is referred to as the bending part 17.

As illustrated in FIG. 15 and FIG. 17, the external connection unit 12 is provided in the bending part 17. By bending the flexible substrate 5 along the bending line 18, the bending part 17 constitutes a side surface of the light irradiation substrate 1 and the external connection unit 12 is positioned on the side surface of the light irradiation substrate 1.

Accordingly, in the present embodiment, among the plurality of cathode wirings 2C, the plurality of anode wirings 2A, the plurality of inter-chip wirings 2I, the dummy patterns 6, the cathode terminal 2CT, and the anode terminal 2AT which are provided on the front surface of the flexible substrate 5 in the developed state as illustrated in FIG. 15, the plurality of cathode wirings 2C, the plurality of anode wirings 2A, the plurality of inter-chip wirings 2I, and the dummy patterns 6 excluding the cathode terminal 2CT and the anode terminal 2AT which are provided in the bending part 17 are arranged so as to be opposed to an affected part.

Hereinafter, for convenience of description, wiring patterns composed of the cathode wirings 2C, the anode wirings 2A, and the inter-chip wrings 2I, and the dummy patterns 6 which are provided on the front surface of the flexible substrate 5 in a state where the flexible substrate 5 is bent are referred to as first electrical conducting material patterns 51 generically.

The flexible substrate 5 is bent in a boundary part (in other words, a boundary part between the external connection unit 12 and the first electrical conducting material patterns 51) between the cathode terminal 2CT and the anode terminal 2AT, and the first electrical conducting material patterns 51.

The front surface of the flexible substrate 5 that is not covered with the anode wirings 2A, the cathode wirings 2C, and the inter-chip wirings 2I in the state where the flexible substrate 5 is bent (that is, a part, which is not covered with the first surface side wirings, on the front surface of the flexible substrate 5 excluding the bending part 17 in the developed state) is covered with the dummy patterns 6, except for the insulating isolation groove 21 which is necessary for insulation and isolation between the adjacent first surface side wirings and between the first surface side wirings and the dummy patterns 6.

Similarly to the first electrical conducting material patterns 15 according to Embodiment 1, coverage (area coverage) of the first electrical conducting material pattern 51 at least in a region surrounded by the LED chips 4 on the front surface of the flexible substrate 5 is preferably 85% or more, and more preferably 90% or more also in the present embodiment.

Moreover, also in the present embodiment, in order to reflect light reflected by an affected part as much as possible and return the light to the affected part for suppressing a loss of light to a minimum, a high reflectance material having total light flux reflectance of 80% or more, or desirably a high reflectance material having total light flux reflectance of 90% or more is used for art least front surfaces of at least the wirings on the front surface side (first surface side wirings) of the flexible substrate 5, which are arranged so as to be opposed to an affected part (that is, at least front surfaces of the cathode wirings 2C, the anode wirings 2A, and the inter-chip wirings 2I).

Moreover, for a similar reason, the same material as those of the anode wirings 2A, the cathode wirings 2C, and the inter-chip wirings 2I is used for the dummy patterns 6 as described above.

In the present embodiment, the first electrical conducting material patterns 51, the cathode terminal 2CT, and the anode terminal 2AT are formed on the same surface of the flexible substrate 5 at the same time with the use of the same material (first electrical conducting material).

That is, the cathode terminal 2CT and the anode terminal 2AT serve as a part (terminal unit) of the first surface side wirings. In the present embodiment, for convenience of description, the wiring patterns composed of the cathode wirings 2C, the anode wirings 2A, and the inter-chip wrings 2I, and the dummy patterns 6 which are provided on the front surface of the flexible substrate 5 in the state where the flexible substrate 5 is bent are referred to as the first electrical conducting material patterns 51 generically as described above, but first electrical conducting material patterns formed of the first electrical conducting material also include the cathode terminal 2CT and the anode terminal 2AT in addition to the first electrical conducting material patterns 51. Accordingly, in a case where the first electrical conducting material patterns are referred to with the cathode terminal 2CT and the anode terminal 2AT included, for convenience of description, the first electrical conducting material patterns 51, the cathode terminal 2CT, and the anode terminal 2AT are referred to as first electrical conducting material patterns 52 generically. That is, the first electrical conducting material patterns 52 include the first electrical conducting material patterns 51.

Note that, in the present embodiment, in order to improve reflectance, the first electrical conducting material patterns 52 are formed of the copper plating layer 22 whose front surface is covered with the silver plating layer 20 as illustrated in FIG. 17 in the same manner as the first electrical conducting material patterns 15 according to Embodiment 1.

The first electrical conducting material patterns 52 are different from the first electrical conducting material patterns 15 according to Embodiment 1 only in patterns, and are able to be formed by a similar method to that of the first electrical conducting material patterns 15. A copper film may be used for the copper plating layer 22, and one that is obtained by applying silver plating to the copper film, may be used for the first electrical conducting material patterns 52.

Also in the present embodiment, when front surfaces of the first electrical conducting material patterns 52, particularly front surfaces of the first electrical conducting material patterns 51 that are positioned on the front surface of the flexible substrate 5 when the flexible substrate 5 is bent are formed of the reflecting material having total light flux reflectance of 80% or more as described above, and the area coverage of the first electrical conducting material patterns 51 at least in the region surrounded by the LED chips 4 is 85% or more, it is possible to improve intensity of irradiation light.

A connecting method of the LED chips 4 and each of the first surface side wirings (the cathode wirings 2C, the anode wirings 2A, and the inter-chip wirings 2I) which are provided on the front surface side of the flexible substrate 5 in the present embodiment is the same as the connecting method of the LED chips 4 and the wirings 2 in Embodiment 1.

Note that, in the present embodiment, each of the LED chips 4 is connected with the bonding wires 3 to an inter-chip wiring 2I on which the LED chip 4 is mounted and an inter-chip wiring 2I which is adjacent to the inter-chip wiring 2I in the Y direction via the insulating isolation groove 21.

In the present embodiment, as illustrated in FIG. 15 to FIG. 17, a substrate size of the flexible substrate 5 is made to be larger than that of Embodiment 1 so as to be 40 mm×45 mm, and 64 pieces of LED chips 4 which are composed of eight rows×eight columns are arranged in total at a pitch of 5 mm in both of the X direction and the Y direction (that is, Px=Py=5 mm).

Moreover, the LED chips 4 are not connected simply in series but connected in a manner of combining series connection and parallel connection. As illustrated in FIG. 15, each two LED chips 4 are provided so as to be arrayed side by side in the Y direction on the front surface side of the flexible substrate 5 between the trunk wiring of each of the cathode wirings 2C and each of the anode wirings 2A which are next to each other in the Y direction, and each of the inter-chip wirings 2I is electrically connected to the cathode wiring 2C and the anode wiring 2A with the bonding wires 3 which are connected to the LED chips 4, and thereby the each two pieces are connected in series. Thus, as illustrated in FIG. 16, 32 LED chips 4 among the 64 LED chips 4 are connected to a cathode side in parallel by the rear cathode wiring 10C which is electrically connected to the cathode terminal 2CT and the cathode wirings 2C via the connection holes 9, whereas the remaining 32 LED chips 4 are connected to an anode side in parallel by the rear anode wiring 10A which is electrically connected to the anode terminal 2AT and the anode wirings 2A via the connection holes 9.

Note that, although a case where each two pieces of the LED chips 4 are connected in series in the Y direction is illustrated as an example in the present embodiment, a configuration in which three or more LED chips 4 are connected in series in the Y direction may be provided by arranging a plurality of inter-chip wirings 2I, on each of which the LED chip 4 is mounted, along the Y direction between the cathode wiring 2C and the anode wiring 2A which are adjacent in the Y direction and electrically connecting the inter-chip wirings 2I by the bonding wires 3. On the contrary, a configuration in which no inter-chip wiring 2 is included and all of the LED chips 4 are connected in parallel may be provided.

Moreover, although a case where each of the cathode wirings 2C has the comb-like shape and each of the LED chips 4 is mounted on each of the branch wirings of each of the cathode wirings 2C is taken as am example for description, a configuration in which each of the anode wirings 2A has a comb-like shape and each of the LED chips 4 is mounted on each branch wiring of each of the anode wirings 2A may be provided.

In the light irradiation substrate 1 according to the present embodiment, the rear cathode wiring 10C and the rear anode wiring 10A each of which has a comb-like shape are arranged as the second surface side wirings on the rear-surface of the flexible substrate 5 in an opposing manner so as to be engaged with each other as illustrated in FIG. 16.

More specifically, each of the rear cathode wiring 10C and the rear anode wiring 10A has the comb-like shape formed by a trunk wiring (trunk line) provided so as to extend in the Y direction and a plurality of branch wirings (branch lines) which branch and extend from the trunk wiring in the X direction. The branch wirings of the rear cathode wiring 10C and the branch wirings of the rear anode wiring 10A are arranged so as to be arrayed alternately in the Y direction.

The plurality of connection holes 9 passing through the flexible substrate 5 are provided in the flexible substrate 5 as illustrated in FIG. 15 to FIG. 17.

The cathode wirings 2C and the cathode terminal 2CT are connected to the rear cathode wiring 10C via the connection holes 9. The anode wirings 2A and the anode terminal 2AT are connected to the rear anode wiring 10A via the connection holes 9 other than the connection holes 9 via which the cathode wirings 2C and the cathode terminal 2CT and the rear cathode wiring 10C are connected.

In the present embodiment, a stainless layer is used for the rear cathode wiring 10C and the rear anode wiring 10A. However, the present embodiment is not limited thereto, and copper, an aluminum film formed of aluminum which is a high reflectance material, or the like may be used for the second surface side wirings.

According to the present embodiment, since the second surface side wirings (that is, the rear cathode wiring 10C and the rear anode wiring 10A) which are formed of a reflecting material, preferably a reflecting material having total light flux reflectance of 80% or more, more preferably a reflecting material (high reflectance material) having total light flux reflectance of 90% or more is formed on the rear surface of the flexible substrate 5, it is possible to reflect light (specifically, light reflected by an affected part side) leaking out from the insulating isolation groove 21 to the rear surface side of the flexible substrate 5 by the second surface side wirings and return the light to the affected part side.

Moreover, in the present embodiment, in order to prevent short circuit between the rear cathode wiring 10C and the rear anode wiring 10A, the rear surface protection film 14 is provided on the whole of the rear surface of the flexible substrate 5 in the developed state, which includes the bending part 17, as an insulating protection film, that covers the rear cathode wiring 10C and the rear anode wiring 10A, as illustrated in FIG. 17.

However, the present embodiment is not limited thereto, and, in a case where it is possible to guarantee that the light irradiation substrate 1 is covered with a holding tool or the like for fixation when the light irradiation substrate 1 is used, the aforementioned rear surface protection film 14 may not be provided.

On the other hand, the wiring protection film 7 is provided on the front surface side of the flexible substrate 5 in order to protect the first surface side wirings, the LED chips 4, the bonding wires 3, and the like. Note that, differently from Embodiment 1, in the present embodiment, each of the LED chips 4 and the bonding wires 3 connected to the LED chip 4 are not covered with each of the LED protective resin domes 8, the wiring protection film 7 is provided on the whole of the rear surface of the flexible substrate 5 in the developed state, which excludes connection parts with the external connection unit 12 in the anode terminal 2AT and the cathode terminal 2CT in the bending part 17.

As illustrated in FIG. 15 and FIG. 17, in the bending part 17, openings 7a are provided in the wiring protection film 7 so that the connection parts with the external connection unit 12 in the anode terminal 2AT and the cathode terminal 2CT are exposed.

Moreover, the front surface of the flexible substrate 5 (that is, a part of the front surface of the flexible substrate 5 in the developed state, which excludes the bending part 17), which is arranged so as to be opposed to an affected part, is covered with the spacer 32 in the present embodiment.

As an example, silicone resin whose thickness is about 0.6 mm is used for the wiring protection film 7 in the present embodiment. Moreover, for the spacer 32, a resin plate made from polystyrene elastomer molded in a square having a thickness of 5 mm and a size of about 40 mm is used as a spacer material. That is, in the present embodiment, T/D is set to satisfy 5.6 mm/5.0 mm=1.1. Note that, T here also includes the thickness of the wiring protection film 7.

Note that, the present embodiment is not limited thereto, and various types of transparent and flexible resin, such as polyurethane resin and silicone rubber may be used as the spacer material. As described in Embodiment 1, one obtained, by filling a plastic bag, which is processed so as to maintain a constant thickness, with water or air, an epoxy resin plate which is transparent and flexible, a water-absorbing polymer processed in a plate shape, or the like may be used.

Needless to say, polystyrene elastomer, silicone rubber, or the like may be used for the spacer 32 in Embodiment 1.

Exemplary Embodiment 7

In the present exemplary embodiment, in order to verify an effect of the light irradiation substrate 1, an experiment similar to that of the exemplary embodiment 1 was performed, except that, in the exemplary embodiment 1, an ulcer in a round shape whose diameter was about 30 mm was formed as the affected part 33 on the skin 31 of the back of each of two mice 30 used for an experiment, the affected part 33 was infected with "MRSA", and the light irradiation substrate 1 illustrated in FIG. 15 to FIG. 17 was used instead of the light irradiation substrate 1 according to Embodiment 1.

Note that, in the present exemplary embodiment, the flexible substrate 5 was enlarged up to 40 mm×45 mm, so that treatment for an affected part having a larger area was enabled. In the present exemplary embodiment, intensity of light irradiation was within a range of ±5% in a region of 20 mm×20 mm in the center part of the flexible substrate 5. Moreover, the intensity of light irradiation was within a range of ±15% even in a region of the diameter of 30 mm, which faces the affected part 33, so that uniformity of the intensity of light irradiation was able to be secured. Additionally, the same effect as that of the exemplary embodiment 1 was achieved also in the present exemplary embodiment.

Note that, the intensity of light irradiation being in the range of ±5% or ±15% here means that a range from a maximum value to a minimum value of the intensity of light irradiation in a target range, which also includes a difference between a part immediately under the LED chip 4 and a part immediately under a middle part between the LED chips 4, is within the range of ±5% or ±15%.

The difference between intensity of light irradiation in the part immediately under the LED chip 4 and intensity of light irradiation in the part immediately under the middle part between the LED chips 4 is able to be almost eliminated by appropriately setting a distance between the LED chips 4 and a surface to be irradiated which is the affected part by the spacer 32. In the middle part between the LED chips 4, though light from one LED chip 4 is weak, when light from the other LED chip 4 is added, it is possible to obtain intensity of light irradiation which is equivalent to that of the part immediately under the LED chip 4.

However, in a peripheral part of the flexible substrate 5, no LED chip 4 exists outside thereof, and thus no light comes from the outside, so that intensity of light irradiation is lowered compared with that of the center part of the flexible substrate 5 even in the part immediately under the LED chip 4. Therefore, compared with the region of 20 mm×20 mm in the center part of the flexible substrate 5, the minimum value of intensity of light irradiation in the region of the diameter of 30 mm is smaller.

Moreover, according to the present exemplary embodiment, by enhancing parallelism of connection of the LED chips 4 as described above, a power source voltage supplied to the light irradiation substrate 1 was able to be reduced. In the present exemplary embodiment, the LED chips 4 were able to be operated with 6.0 V to 6.5 V, and the power source voltage is able to be supplied from, for example, an inexpensive and compact AC adaptor or battery box each of which is not illustrated.

Further, in the present exemplary embodiment, by providing the external connection unit 12 on the front surface of the flexible substrate 5, that is, on the same surface as a mounting surface of the LED chips 4 in the flexible substrate 5 in the developed state as illustrated in FIG. 15, a mounting process of the LED chips 4 and the external connection unit 12 which is carried out after a double-sided wiring substrate in which wirings are provided in both of the front and rear surfaces of the flexible substrate 5 is completed is finished by processing only for the front surface of the flexible substrate 5.

As described above, in the present embodiment, the cathode terminal 2CT and the anode terminal 2AT which serve as the connection parts with the external connection unit 12 are provided on the front surface of the flexible substrate 5. Thus, according to the present embodiment, compared with a case where the LED chips 4 are mounted on the front surface of the flexible substrate 5, the LED chips 4 and the first surface side wirings are connected with the bonding wires 3, and thereafter resin sealing is performed and lead wires are soldered as the external connection unit 12 on the rear surface of the flexible substrate 5, a force applied to the LED chips 4 and the bonding wires 3 on the front surface of the flexible substrate 5 is suppressed. Moreover, it is difficult for heat at a time of soldering the external connection unit 12 to be transferred to the first surface side wirings.

Thus, according to the present embodiment, it is possible to suppress occurrence of failure such as disconnection resulting from a force applied to the LED chips 4 and the bonding wires 3 on the front surface of the flexible substrate 5 at the time of soldering the external connection unit 12 or discoloration of the first surface side wirings due to the heat at the time of soldering the external connection unit 12. Actually, such failure rarely occurred in the present exemplary embodiment.

Moreover, according to the present exemplary embodiment, by bending the end of the flexible substrate 5 in which the cathode terminal 2CT and the anode terminal 2AT that serve as the connection parts with the external connection unit 12 are arranged, even in a case where the spacer 32 is provided between the light irradiation substrate 1 and an affected part, it is possible to easily perform wiring connection at a time of treatment without being obstructed by the spacer 32 when connecting the external connection unit 12 and a power source.

Thus, according to the present embodiment, without increasing time and effort for wiring connection at a time of treatment, production of the light irradiation substrate 1 was facilitated, the yield was improved, and costs of production of the light irradiation substrate 1 was succeeded in reduction.

Modified Example

Note that, in the present embodiment, description has been given by taking, as an example, a case of bending the end of the flexible substrate 5 in the longitudinal direction, in which the external connection unit 12 is arranged. However, the present embodiment is not limited thereto, and, in a case where the light irradiation substrate 1 is fixed (held) to an affected part, for example, by a fixing tool such as a bandage, it is not necessary to bend the flexible substrate 5. For example, the entirety of the light irradiation substrate 1 may be covered with the spacer 32, so that lead wires which are used as the external connection unit 12 are drawn out from a space between the spacer 32 and the flexible substrate 5.

Moreover, similarly to Embodiment 1, the dummy patterns 6 are not always necessary also in the present embodiment. For example, it is also possible to cover the whole of the front surface of the flexible substrate 5 with the first surface side wirings (the cathode wirings 2C, the anode wirings 2A, and the inter-chip wirings 2I, in the present embodiment), except for the insulating isolation groove 21 and the peripheral part of the flexible substrate 5.

Embodiment 8

Still another embodiment of the invention will be described as follows on the basis of FIG. 18. Note that, in the present embodiment, description will be given for a different point from Embodiments 1 to 7, the same reference signs are assigned to constituents having the same functions as those of the constituents described in Embodiments 1 to 7, and description thereof is omitted.

Figure 18:
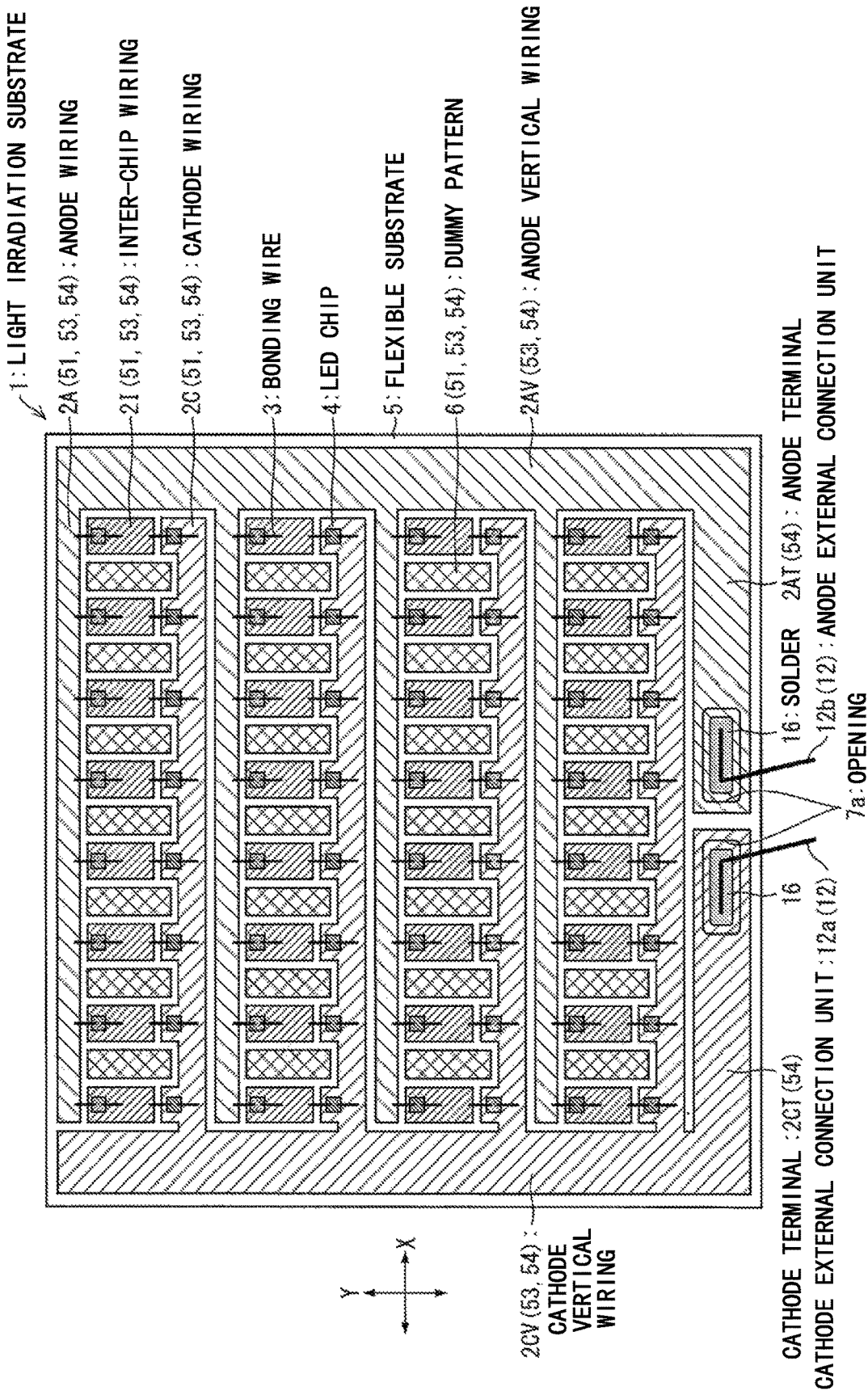
FIG. 18 is a schematic front surface view illustrating a configuration of a light irradiation substrate according to Embodiment 8 of the invention.

FIG. 18 is a schematic front surface view illustrating a configuration of the light irradiation substrate 1 according to the present embodiment.

The light irradiation substrate 1 according to the present embodiment is the same as the light irradiation substrate 1 according to Embodiment 7, except that a cathode vertical wiring 2CV and an anode vertical wiring 2AV are provided on the front surface of the flexible substrate 5 instead of the rear cathode wiring 10C and the rear anode wiring 10A which are the second surface side wirings so that the wirings are completed only on the front surface side of the flexible substrate 5.

That is, the light irradiation substrate 1 according to the present embodiment includes the flexible substrate 5, the plurality of cathode wirings 2C (wiring patterns, first surface side wirings, second cathode wirings), the plurality of anode wirings 2A (wiring patterns, first surface side wirings, second anode wirings), the plurality of inter-chip wirings 2I (wiring patterns, first surface side wirings), the cathode vertical wiring 2CV (wiring pattern, first surface side wiring, first cathode wiring), the anode vertical wiring 2AY (wiring pattern, first surface side wiring, inter-wiring wiring, first anode wiring), the cathode terminal 2CT (terminal unit), the anode terminal 2AT (terminal unit), the dummy patterns 6, the plurality of LED chips 4 (light-emitting elements), the plurality of bonding wires 3, the wiring protection film 7, the external connection unit 12 composed of the cathode external connection unit 12a and the anode external connection unit 12b, and, as necessary, the spacer 32, as illustrated in FIG. 18.

Note that, in the present embodiment, description will be given by taking, as an example, the case where the entirety of the light irradiation substrate 1 is covered with the spacer 32 and lead wires which are used as the external connection unit 12 are drawn out from a space between the spacer 32 and the flexible substrate 5 as described in the modified example in Embodiment 7.

In the present embodiment, the anode external connection unit 12b and the cathode external connection unit 12a are connected similarly to Embodiment 7, and extend to an outside from the space between the spacer 32 and the flexible substrate 5.

Moreover, the second surface side wirings are not provided in the light irradiation substrate 1 according to the present embodiment. Therefore, differently from the flexible substrate 5 according to Embodiment 7, the connection holes 9 are not provided in the flexible substrate 5, and neither the rear cathode wiring 10C and the rear anode wiring 10A nor the rear surface protection film 14 is provided in the flexible substrate 5.

Note that, in the light irradiation substrate 1 according to the present embodiment, the wiring protection film 7 and the spacer 32 (refer to FIG. 17) are provided on the front surface side of the flexible substrate 5 similarly to Embodiment 7. Note that, for convenience of illustration, as to the wiring protection film 7, only the openings 7*a* by which the cathode terminal 2CT and the anode terminal 2AT are exposed are illustrated in FIG. 18.

Moreover, illustration of the spacer 32 is omitted in FIG. 18. Similarly to Embodiment 1, also in the present embodiment, the spacer 32 may be provided integrally with the light irradiation substrate 1, or may be provided separately from the light irradiation substrate 1. That is, the light irradiation substrate 1 may be a light irradiation substrate with a spacer, or may be provided separately from the spacer 32.

The cathode vertical wiring 2CV and the anode vertical wiring 2AV are arranged along the Y direction in both ends of the flexible substrate 5 in the X direction so as to face each other with an arrangement region of the first electrical conducting patterns 51 (region surrounded by the LED chips 4) and wire connection parts with the external connection unit 12 in the cathode terminal 2CT and the anode terminal 2AT held therebetween as illustrated in FIG. 18.

A function which is included in the rear cathode wiring-10C and the rear anode wiring 10A in Embodiment 7 is included in the cathode vertical wiring 2CV and the anode vertical wiring 2AV in the present embodiment.

As illustrated in FIG. 18, the cathode wirings 2C, the anode wirings 2A, the inter-chip wirings 2I, the dummy patterns 6, the cathode vertical wiring 2CV, the anode vertical wiring 2AV, the cathode terminal 2CT, and the anode terminal 2AT which are provided on the front surface of the flexible substrate 5 and adjacent to each other are insulated and isolated from each other by the insulating isolation groove 21.

However, the cathode vertical wiring 2CV is connected to the cathode terminal 2CT, and each of the cathode wirings 2C is connected to the cathode vertical wiring 2CV in a comb-like manner (comb teeth manner) so as to branch off in the X direction from the cathode vertical wiring 2CV which is provided so as to extend in the Y direction.

The anode vertical wiring 2AV is connected to the anode terminal 2AT, and each of the anode wirings 2A is connected to the anode vertical wiring 2AV in a comb-like manner (comb teeth manner) so as to branch off in the X direction from the anode vertical wiring 2AV which is provided so as to extend in the Y direction.

A wiring pattern formed by the cathode vertical wiring 2CV and the plurality of cathode wirings 2C in the comb-like manner and a wiring pattern formed by the anode vertical wiring 2AV and the plurality of cathode wirings 2C in the comb-like manner are arranged so as to be opposed and engages with each other.

Similarly to Embodiment 7, each of the inter-chip wirings 2I is provided so as to be opposed to each of branch wirings of each of the cathode wirings 2C also in the present embodiment. Moreover, each of the LED chips 4 is mounted on each of the branch wirings of each of the cathode wirings 2*c* and on each of the inter-chip wirings 2I, and each two LED chips 4 are provided side by side in the Y direction between a trunk wiring of each of the cathode wirings 2C and each of the anode wirings 2A which are adjacent in the Y direction.

Then, each of the inter-chip wirings 2I is electrically connected to each of the cathode wirings 2C and each of the anode wirings 2A with the bonding wires 3 connected to each of the LED chips 4.

Thereby, similarly to Embodiment 7, also in the present embodiment, as illustrated in FIG. 18, each two LED chips 4 are connected in series in the Y direction, and 32 LED chips 4 among 64 LED chips 4 are connected in parallel by the wiring pattern which is formed into the comb-like shape by the cathode vertical wiring 2CV connected to the cathode terminal 2CT and the plurality of cathode wirings 2C. Moreover, the remaining 32 LED chips 4 are connected in parallel by the wiring pattern which is formed into the comb-like shape by the anode vertical wiring 2AV connected to the anode terminal 2AT and the plurality of cathode wirings 2C.

Note that, also in the present embodiment, by arranging a plurality of inter-chip wirings 2I, on each of which the LED chip 4 is mounted, along the Y direction between the cathode wiring 2C and the anode wiring 2A which are adjacent in the Y direction and electrically connecting the inter-chip wirings 2I with the bonding wires 3, it is possible to connect three or more LED chips 4 in series in the Y direct ion, similarly to Embodiment 7.

Moreover, also in the present embodiment, similarly to Embodiment 7, a configuration in which the anode wirings 2A has the comb-like shape and each of the LED chips 4 is mounted on each of the branch wirings of each of the anode wirings 2A may be provided, and each of the LED chips 4 is required only to be mounted, for example, at least on each of the inter-chip wirings 2I among the cathode wirings 2C, the anode wirings 2A, and the inter-chip wirings 2I.

In the light irradiation substrate 1 according to the present embodiment, a light-emitting region surrounded by the LED chips 4 is hardly changed from, that of the light irradiation substrate 1 according to Embodiment 1. However, a width of the light irradiation substrate 1 according to the present embodiment is increased from, that of the light irradiation substrate 1 according to Embodiment 1 by about 10 mm. As a size of an affected part, a region whose diameter is up to about 30 mm is able to be dealt with.

In a case of Embodiment 7, a distance between the LED chip 4 in an outermost periphery and a substrate end of the flexible substrate 5 which faces the LED chip 4 (that is, a shortest distance from the LED chip 4 in the outermost periphery to the substrate end of the flexible substrate 5) is snort in any side of the light irradiation substrate 1 as illustrated in FIG. 15. Accordingly, by arranging a plurality of light irradiation substrates 1 in a tiles-like form so as to be in contact with each other, it was possible to give treatment to a larger affected part. Note that, in a case where the light irradiation substrate 1 is used in such a manner, it is preferable that the distance between the LED chip 4 in the outermost periphery and the substrate end of the flexible substrate 5 is approximately half of a distance between adjacent LED chips 4 (that is, the average value D of pitches between adjacent LED chips 4).

However, in the present embodiment, the cathode vertical wiring 2CV and the anode vertical wiring 2AV are in the both ends of the flexible substrate 5 in the X direction as illustrated in FIG. 18. Therefore, the distance between the LED chip 4 in the outermost periphery and the substrate end of the flexible substrate 5 is longer in the both ends of the flexible substrate 5 in the X direction. Accordingly, in a case where a plurality of light irradiation substrates 1 illustrated in FIG. 18 are horizontally arranged side by side, light intensity is reduced in a connection part of the adjacent light irradiation substrates 1. Also in a case where another light irradiation substrate 1 is arranged in a horizontal direction so as to be adjacent to a side (in FIG. 18, an upper side of the light irradiation substrate 1) other than a side in which the cathode vertical wiring 2CV is arranged, a side in which the anode vertical wiring 2AV is arranged, and a side in which the cathode terminal 2CT and the anode terminal 2AT are arranged, such reduction in light intensity is not caused, but arrangement of the light irradiation substrates 1 is restricted compared with that of Embodiment 7.

In the present embodiment, the light irradiation substrate 1 is able to have a one-side wiring structure in which the wirings are provided only on one side of the flexible substrate 5, so that it is possible to reduce costs of manufacturing the light irradiation substrate 1. Note that, this point is the same as Embodiment 3. Thus, according to the present embodiment, it is possible to provide a most inexpensive product as a light irradiation substrate (light irradiation device) which is independent and used for treatment for an affected part having a relatively small area.

Moreover, in the present embodiment, the cathode wirings 2C, the anode wirings 2A, the inter-chip wirings 2I, the cathode vertical wiring 2CV, the anode vertical wiring AV, the dummy patterns 6, the cathode terminal 2CT, and the anode terminal 2AT are formed on the same surface of the flexible substrate 5 at the same time by using the same material (first electrical conducting material). Hereinafter, for convenience of description, the cathode wirings 2C, the anode wirings 2A, the inter-chip wirings 2I, the cathode vertical wiring 2CV, the anode vertical wiring 2AV, the dummy patterns 6, the cathode terminal 2CT, and the anode terminal 2AT are referred to as first electrical conducting material patterns 54 generically. In addition, the first electrical conducting material patterns 54 excluding the cathode terminal 2CT and the anode terminal 2AT (that is, the cathode wirings 2C, the anode wirings 2A, the inter-chip wirings 2I, the cathode vertical wiring 2CV, the anode vertical wiring 2AV, and the dummy patterns 6) are referred to as first electrical conducting material patterns 53 generically. That is, the first electrical conducting material patterns 54 include the first electrical conducting material patterns 53.

In the present embodiment, in order to improve reflectance, the first electrical conducting material patterns 54 are formed of the copper plating layer 22 whose front surface is covered with the silver plating layer 20 as illustrated in FIG. 17 in the same manner as the first electrical conducting material patterns 15 and 52.

The first electrical conducting material patterns 54 are different from the first electrical conducting material patterns 15 and 52 only in patterns, and are able to be formed by a method similar to those of the first electrical conducting material patterns 15 and 52. Note that, a copper film may be used as the copper plating layer 22, and one that is obtained by applying silver plating to the copper film may be used as the first electrical conducting material patterns 54.

As described above, also in the present embodiment, when front surfaces of the first electrical conducting material patterns 54, particularly front surfaces of the first electrical conducting material patterns 53 are formed of a reflecting material having total light flux reflectance of 80% or more, and area coverage of the first electrical conducting material patterns 51 (in the example illustrated in FIG. 18, the cathode wirings 2C, the anode wirings 2A, the inter-chip wirings 2I, and the dummy patterns 6) which are the first electrical conducting material patterns 53 at least in a region surrounded by the LED chips 4 is 85% or more, it is possible to improve intensity of irradiation light.

Modified Example

Note that, also in the present embodiment, the dummy patterns 6 are not always necessary. For example, it is possible to cover the whole of the front surface of the flexible substrate 5 with the cathode wirings 2C, the anode wirings 2A, the inter-chip wirings 2I, the cathode vertical wiring 2CV, the anode vertical wiring 2AV, the cathode terminal 2CT, and the anode terminal 2AT, except for the insulating isolation groove 21 and the outer periphery of the flexible substrate 5.

In addition, in the present embodiment, the entirety of the light irradiation substrate 1 is covered with the spacer 32 and the lead wires which are used as the external connection unit 12 are drawn out from the space between the spacer 32 and the flexible substrate 5 as described above, but a configuration in which the end of the flexible substrate 5 in the longitudinal direction, in which the external connection unit 12 is arranged, is bent may be provided similarly to Embodiment 7.

CONCLUSION

A light irradiation substrate (the light irradiation substrate 1, the light irradiation substrate with a spacer 35) according to an aspect 1 of the invention includes: a flexible substrate that is insulating; first electrical conducting material patterns (the first electrical conducting material patterns 15 (the wirings 2 or the wirings 2 and the dummy pattern 6), the first electrical conducting material patterns 51 (the cathode wirings 2C, the anode wirings 2A, and the inter-chip wirings 2I, or the cathode wirings 2C, the anode wirings 2A, the inter-chip wirings 2I, and the dummy patterns 6), the first electrical conducting material patterns 52 (the first electrical conducting material patterns 51, the cathode terminal 2CT, and the anode terminal 2AT), the first electrical conducting material patterns 53 (the first electrical conducting material patterns 51, the cathode vertical wiring 2CV, and the anode vertical wiring 2AV), or the first electrical conducting material patterns 54 (the first electrical conducting material patterns 53, the cathode terminal 2CT, and the anode terminal 2AT)) that are provided on a first surface of the flexible substrate; and light-emitting elements (LED chips 4) that are mounted on at least a part of the first electrical conducting material patterns, in which front surfaces of the first electrical conducting material patterns are formed of a reflecting material total light flux reflectance of which is 80% or more, and area coverage of the first electrical conducting material patterns (the first electrical conducting material patterns 15 or the first electrical conducting material patterns 51) at least in a region surrounded by the light-emitting elements is 85% or more.

Note that, in this case, the total light flux reflectance does not mean reflectance of specular reflection but a ratio of light energy obtained by integrating all reflected light, which is diffused and reflected, to energy of entering light. Moreover, the area coverage of the first electrical conducting material patterns in the region surrounded by the light-emitting elements means an area ratio of a region, which is covered with the first electrical conducting material patterns, in an area of the region surrounded by the light-emitting elements in the first surface of the flexible substrate 5.

An irradiation area of an existing light source of a lamp type is too large for am affected part which is about several cm and whose area is relatively small, so that there is a concern about various side effects on a normal part. However, according to the aforementioned configuration, by using the light-emitting elements which are provided on the first surface of the flexible substrate 5 as light sources, it is possible to cover only an affected part and perform light irradiation, thus making it possible to make a patient less restrained and suppress a burden of the patient to a minimum. Moreover, mounting the light-emitting elements on the flexible substrate 5 allows suitable usage also for an affected part having a curved surface such as an arm or a foot.

Moreover, a wiring material is required to have a low resistance and have high reflectance of a front surface thereof. Particularly, in order to reduce a loss during light irradiation, it is necessary to minimize an energy loss due to reflection. Thus, the total light flux reflectance needs to be 80% or more as described above.

According to the present aspect, the front surfaces of the first electrical conducting material patterns are formed of the reflecting material total light flux reflectance of which is 80% or more, so that it is possible to reflect light reflected from an affected part as much as possible to return the light to the affected part, and to suppress the loss of light to a minimum.

Moreover, in order to enhance efficiency of light irradiation, it is important that the first electrical conducting material patterns cover the front surface of the flexible substrate 5 over an area as wide as possible. Thus, it is desirable that the area coverage of the first electrical conducting material patterns at least in the region surrounded by the light-emitting elements is 85% or more.

According to the present aspect, as described above, the front surfaces of the first electrical conducting material patterns are formed of the reflecting material total light flux reflectance of which is 80% or more, and the area coverage of the first electrical conducting material patterns at least in the region surrounded by the light-emitting elements is 85% or more, and it is thereby possible to improve intensity of irradiation light.

Accordingly, the light irradiation substrate is suitable for treatment for a relatively small diseased part, and is able to realize almost uniform and efficient light irradiation even for an affected part that is not flat without forcing a patient to take an unnatural posture as an irradiation device of a lamp type. In addition, by using the light irradiation substrate, it is possible to improve intensity of irradiation light as described above, so that treatment time is able to be shortened. Thus, according to the aforementioned configuration, it is possible to suppress a side effect due to light irradiation to a minimum and suppress a physical burden, a mental burden, an economic burden, and the like of a patient and his/her family.

Note that, PTL 3 discloses that a reflection layer is provided around a light emitter, but includes no description about supply of power to the light emitter, and does not disclose a relation between wirings and the reflection layer at all.

Moreover, in PTL 3, the reflection layer is provided completely separately from the light emitter, so that it is difficult to arrange the reflection layer without making a hole in a part corresponding to the light emitter.

However, in the present aspect, since the light-emitting elements are formed on at least a part of the first electrical conducting material patterns, it is not necessary to make a hole in a reflection layer. Moreover, in the present aspect, since the area coverage of the first electrical conducting material patterns at least in the region surrounded by the light-emitting elements is 85% or more, not only a periphery of each of the light-emitting elements but also at least the most part of the region surrounded by the light-emitting elements in the front surface of the flexible substrate 5 is covered with the reflecting material total light flux reflectance of which is 80% or more. Thus, it is possible to realize light irradiation which is greatly effective to improve intensity of irradiation light and almost uniform and efficient.

A light irradiation substrate (the light irradiation substrate 1, the light irradiation substrate with a spacer 35) according to an aspect 2 of the invention may include, on a second surface opposite to the first surface in the flexible substrate 5, a light shielding member (a reflecting member, a light absorbing member, for example, the rear surface reflection film 13, the rear wirings 10, an opaque resin film, the rear cathode wiring 10C, the rear anode wiring 10A) that prevents light from leaking out from a side of the second surface, in the aspect 1.

On the front surface of the flexible substrate 5, there is a gap (the insulating isolation groove 21) for insulation and isolation between the first electrical conducting material patterns (for example, between the wirings 2, between the wirings 2 and the dummy pattern 6, between the cathode wirings 2C, the anode wirings 2A, the inter-chip wirings 21, the dummy pattern 6, the cathode terminal 2CT, and the anode terminal 2AT which are adjacent to each other, or between the cathode wirings 2C, the anode wirings 2A, the inter-chip wirings 2I, the dummy patterns 6, the cathode vertical wiring 2CV, the anode vertical wiring 2AV, the cathode terminal 2CT, and the anode terminal 2AT which are adjacent to each other (note that, the cathode terminal 2CT and the cathode vertical wiring 2CV are connected to (integrated with) each other and the cathode vertical wiring 2CV and the cathode wirings 2C are connected to (integrated with) each other, and the anode terminal 2AT and the anode vertical wiring 2AV are connected to each other and the anode vertical wiring 2AV and the anode wirings 2A are connected to each other)). Thus, light slightly leaks out to the rear surface side of the flexible substrate 5 through the gap between the first electrical conducting patterns.

Then, by providing the light shielding member on the second surface as described above, it is possible to prevent the light leakage from the side of the second surface.

Thus, it is possible to eliminate light leakage to an outside during treatment, and to reduce a burden of eyes of a patient or a surrounding person such as his/her family. In addition, since it is unnecessary to consider a surrounding person as to the leakage of light, it is also possible to reduce a mental burden of the patient or his/her family.

In a light irradiation substrate (the light irradiation substrate 1, the light irradiation substrate with a spacer 35) according to an aspect 3 of the invention, the light shielding member may be a reflecting member (for example, the rear surface reflection film 13, the rear wirings 10, the rear cathode wiring 10C, or the rear anode wiring 10A) in the aspect 2.

By forming the reflecting member as the light shielding member, it is possible to reflect light leaking out to the rear surface side of the flexible substrate 5 from the gap between the first electrical conducting material patterns (specifically, light reflected from a side of an affected part) by the reflecting member and return the light to the affected part.

In a light irradiation substrate (the light irradiation substrate 1, the light irradiation substrate with a spacer 35) according to an aspect 4 of the invention, the light shielding member (for example, the rear surface reflection film 13, the rear wirings 10, the rear cathode wiring 10C, or the rear anode wiring 10A) may be formed of a reflecting material total light flux reflectance of which is 80% or more in the aspect 3.

According to the aforementioned configuration, it is possible to reflect light reflected from a side of an affected part as much as possible and return the light to the affected part, and suppress a loss of light to a minimum.

In a light irradiation substrate (the light irradiation substrate 1, the light irradiation substrate with a spacer 35) according to an aspect 5 of the invention, the light shielding member may be a light absorbing member (for example, an opaque resin film) in the aspect 2.

Also in this case, it is possible to prevent light from leaking out from the rear surface side of the flexible substrate 5, thus making it possible to eliminate light leakage to an outside during treatment.

In a light irradiation substrate (the light irradiation substrate 1, the light irradiation substrate with a spacer 35) according to an aspect 6 of the invention, the flexible substrate 5 may be an opaque substrate in any of the aspects 1 to 5.

Also in this case, it is possible to prevent light from leaking out from, the rear surface side of the flexible substrate 5, thus making it possible to eliminate light leakage to an outside during treatment.

A light irradiation substrate (the light irradiation substrate 1, the light irradiation substrate with a spacer 35) according to an aspect 7 of the invention may include, on the second surface opposite to the first surface in the flexible substrate 5, a second surface side wiring (the rear wirings 10) that is electrically connected to a part of the first electrical conducting material patterns (the wirings 2), in which an external connection unit 12 that is connected to an outside is connected to the second surface side wiring, in any of the aspects 1 to 6.

In this manner, by connecting the external connection unit 12 to the side opposite to a mounting surface of the light-emitting elements in the flexible substrate 5, it is possible to easily connect the external connection unit 12 and the second surface side wiring. Moreover, it is possible to avoid reduction in reflectance, snort circuit, and the like which are caused by a stain on the front surfaces of the first electrical conducting material patterns (the first electrical conducting material patterns 15, for example, the first surface side wirings and the dummy pattern 6), so that it is also possible to avoid reduction in a production yield.

In a light irradiation substrate (the light irradiation substrate 1, the light irradiation substrate with a spacer 35) according to an aspect 8 of the invention, the external connection unit 12 may be connected to a part of the first electrical conducting material patterns (a part of the wirings 2, or the cathode terminal 2CT and the anode terminal 2AT), in any of the aspects 1 to 6.

According to the aforementioned configuration, since the external connection unit 12 is connected to the side of the second surface opposite to the first surface in the flexible substrate 5, it is not necessary to form, on the second surface, the second surface side wiring which is electrically connected to the first electrical conducting material patterns. Thus, compared with a case where the external connection unit 12 is connected to the side of the second surface of the flexible substrate 5, it is possible to simplify the configuration, thus making it possible to provide an inexpensive light irradiation substrate.

In a light irradiation substrate (the light irradiation substrate 1) according to an aspect 9 of the invention, the part of the first electrical conducting material patterns to which the external connection unit 12 is connected may be a terminal unit (the cathode terminal 2CT and the anode terminal 2AT), the terminal unit may be provided in one end of the flexible substrate 5, and the end of the flexible substrate 5, in which the terminal unit, is provided may be bent, in the aspect 8.

According to the aforementioned configuration, at a time of connecting the external connection unit 12 to the terminal unit, for example, by soldering, it is possible to suppress a force to be applied to the light-emitting elements, and suppress heat to be applied to a part of the first electrical conducting material patterns other than the terminal unit, thus making it possible to suppress generating inferior goods. Moreover, it is possible to easily arrange the external connection unit 12. Thus, according to the aforementioned configuration, it is possible to easily produce the light irradiation substrate, and improve the production yield and reduce the production costs.

A light irradiation substrate (the light irradiation substrate 1, the light irradiation substrate with a spacer 35) according to an aspect 10 of the invention may include the spacer 32 that separates the light-emitting elements from an irradiation target (affected part) that is irradiated with light emitted by the light-emitting elements by a constant distance, in which the spacer 32 may transmit light emitted by the light-emitting elements, and may be flexible.

According to the aforementioned configuration, it is possible to irradiate, via the spacer 32, the irradiation target with the light emitted by the light-emitting elements, and maintain the distance between the light-emitting elements and the irradiation target to be constant and fix a positional relation between the light-emitting elements and the irradiation target.

Moreover, the spacer 32 is flexible, and therefore allows suitable usage for an affected part having a curved surface such as an arm or a foot.

In a light irradiation substrate (the light irradiation substrate 1, the light irradiation substrate with a spacer 35) according to an aspect 11 of the invention, the light-emitting elements and a part of the first electrical conducting material patterns (the first electrical conducting material patterns 15) (a part of the wirings 2) on which the light-emitting elements are mounted may be covered with a protection film (the wiring protection film 7 and the LED protective resin domes 8) which are formed of insulating resin, and the spacer 32 may be arranged on the light-emitting elements via the protection film, in the aspect 10.

PTL 5 discloses that a light-transmitting material held between an affected part and the LED is transparent or semitransparent and flexible.

However, PTL 5 emphasizes transfer of heat generated by a light source to an affected part, so that there are some cases where the light source does not face an affected part as FIG. 3 to FIG. 6, FIG. 9, and FIG. 10 of PTL 5. Moreover, in PTL 5, even in a case where the light source faces an affected part, a light-transmitting material is arranged around the light source via a cavity as illustrated in FIG. 2b of PTL 5. Furthermore, in FIG. 8 of PTL 5, there is a cavity between an affected part and the light source.

When an air layer lies between a spacer and a light source in this manner, efficiency of light incidence from the light source on the spacer is considerably deteriorated.

However, according to the present aspect, the spacer 32 is arranged on the light-emitting elements via the protection film as described above, so that it is possible to improve efficiency of light irradiation to an irradiation target.

In a light irradiation substrate (the light irradiation substrate 1, the light irradiation substrate with a spacer 35) according to an aspect 12 of the invention, the spacer 32 may be formed of insulating resin, and the spacer 32 and the protection film may be formed integrally, in the aspect 11.

By forming the spacer 32 and the protection film integrally in this manner, it is possible to facilitate an attaching process compared with a case of separately attaching the light irradiation substrate and the spacer to an irradiation target.

In a light irradiation substrate (the light irradiation substrate 1, the light irradiation substrate with a spacer 35) according to am aspect 13 of the invention, T/D≥0.5 may be satisfied when an average value of pitches between adjacent light-emitting elements is D and an average thickness of the spacer 32 (to be exact, a distance from the front surface of the LED chip 4 to a front surface of the spacer 32) is T, in any of the aspects 10 to 12.

There is a tendency that, when T/D is small, a difference of intensity of light irradiation between a part immediately under the light-emitting element and a part immediately under a middle part between the light-emitting elements becomes large. Thus, it is desirable that T/D is 0.5 or more.

In a light irradiation substrate (the light irradiation substrate 1, the light irradiation substrate with a spacer 35) according to an aspect 14 of the invention, the sensor unit 40 that includes at least one of the optical sensor 41 and the temperature sensor 42 may be provided on the first surface, in any of the aspects 1 to 13.

According to the aforementioned configuration, it is possible to control an electrical current to be supplied to the light-emitting elements on the basis of an output of the sensor unit 40.

In a light irradiation substrate (the light irradiation substrate 1, the light irradiation substrate with a spacer 35) according to an aspect 15 of the invention, the control unit 43 that controls an electrical current to be supplied to the light-emitting elements on the basis of the output of the sensor unit 40 may be provided in the aspect 14.

According to the aforementioned configuration, the light irradiation substrate is able to control supply of power to the light-emitting elements by itself on the basis of the output of the sensor unit 40.

A light irradiation substrate (the light irradiation substrate 1, the light irradiation substrate with a spacer 35) according to an aspect 16 of the invention may have a configuration in which the first electrical conducting patterns are composed of first surface side wirings (the wirings 2; the cathode wirings 2C, the anode wirings 2A, and the inter-chip wirings 2I; or the cathode wirings 2C, the anode wirings 2A, the inter-chip wirings 2I, the cathode vertical wiring 2CV, and the anode vertical wiring 2AV) that supply power to the light-emitting elements and the dummy pattern 6 that is insulated and isolated from the first surface side wirings and covers a region in which the first surface side wirings are not provided, and the first surface side wirings and the dummy pattern are formed of the same material.

According to the present aspect, by forming, with the use of a reflecting material which is the same as that of the first surface side wirings which supply power to the light-emitting elements and has total light flux reflectance of 80% or more, the dummy pattern 6 on which the light-emitting elements are not mounted and which does not contribute to supply power, it is possible to form the first surface side wirings and the dummy pattern 6 at the same time, and reflect light reflected from an affected part as much as possible and return the light to the affected part and suppress a loss of light to a minimum. Thereby, it is possible to improve intensity of irradiation light compared with a case where the front surfaces of the first surface side wirings are not formed of a reflecting material having total light flux reflectance of 80% or more or a case where the dummy pattern 6 is not provided.

Moreover, in a case where the dummy pattern 6 is used, even if a defect is caused in any one place in the insulating isolation groove 21 that performs insulation and isolation between the first surface side wirings and between the first surface side wirings and the dummy pattern 6, failure is rarely caused due to the defect in the one place. Thus, when the first electrical conducting patterns include the dummy pattern 6, it is possible to substantially improve a production yield.

A light irradiation substrate (the light irradiation substrate 1) according to an aspect 17 of the invention may include, on a second surface opposite to the first surface in the flexible substrate 5, a second surface side wiring (the rear cathode wiring 10C, the rear anode wiring 10A) that is electrically connected to the first electrical conducting material patterns, in which a plurality of light-emitting elements may be connected in series by the first electrical conducting patterns in a first direction, and a plurality of light-emitting elements may be connected in parallel by the second surface side wiring in a second direction orthogonal to the first direction, in the aspect 1.

According to the aforementioned configuration, it is possible to enhance parallelism, of connection of the light-emitting elements, so that it is possible to reduce a power source voltage to be supplied to the light irradiation substrate.

In a light irradiation substrate (the light irradiation substrate 1) according to an aspect 18 of the invention, the second surface side wiring may include a first cathode wiring (the rear cathode wiring 10C) in a comb-like shape, which has a trunk wiring provided so as to extend in the first direction and branch wirings each of which is provided so as to branch from the trunk wiring in the second direction, and a first anode wiring (the rear anode wiring 10A) in a comb-like shape, which has a trunk wiring provided so as to extend in the first direction and branch wirings each of which is provided so as to branch from the trunk wiring in the second direction and is arranged so as to be engaged with the first cathode wiring, the first electrical conducting patterns may include a plurality of second cathode wirings (the cathode wirings 2C) and a plurality of second anode wirings (the anode wirings 2A) each of which is provided so as to extend in the second direction and a plurality of inter-wiring wirings (the inter-chip wirings 2I) which are provided between the second cathode wirings and the second anode wirings that are adjacent to each other in the first direction, at least one of the inter-wiring wirings may be provided in the first direction and a plurality of inter-wiring wirings may be provided in the second direction, each of the light-emitting elements may be mounted at least on each of the inter-wiring wirings among the second cathode wirings, the second anode wirings, and the inter-wiring wirings, and each of the inter-wiring wirings may be electrically connected to each of the second cathode wirings and each of the second anode wirings which are adjacent in the first direction with bonding wires connected to the light-emitting element, in the aspect 17.

According to the aforementioned configuration, it is possible to easily realize the light irradiation substrate described in the aspect 17.

In a light irradiation substrate (the light irradiation substrate 1) according to an aspect 19 of the invention, the first electrical conducting patterns may include a first cathode wiring (the cathode vertical wiring 2CV) and a first anode wiring (the anode vertical wiring 2AV) each of which is provided so as to extend in the first direction, a plurality of second cathode wirings (the cathode wirings 2C) which are connected to the first cathode wiring and provided so as to extend in a second direction that is orthogonal to the first direction, a plurality of second anode wirings (the anode wirings 2A) which are connected to the first anode wiring and provided so as to extend in the second direction, and a plurality of inter-wiring wirings (the inter-chip wirings 2I) each of which is provided between each of the second cathode wirings and each of the second anode wirings that are adjacent to each other in the first direction, the second cathode wirings and the second anode wirings may be arranged alternately in the first direction, the plurality of inter-wiring wirings may be provided in the second direction so that at least one of the inter-wiring wirings is provided in the first direction, each of the light-emitting elements may be mounted at least on each of the inter-wiring wirings among the second cathode wirings, the second anode wirings, and the inter-wiring wirings, each of the inter-wiring wirings may be electrically connected to each of the second cathode wirings and each of the second anode wirings which are adjacent in the first direction with bonding wires connected to the light-emitting element, and a plurality of light-emitting elements may be connected in series in the first direction with the bonding wires and a plurality of light-emitting elements may be connected in parallel with the plurality of second cathode wirings connected to the first cathode wiring and the plurality of second anode wirings connected to the first anode wiring, in the aspect 1.

According to the aforementioned configuration, it is possible to enhance parallelism of connection of the light-emitting elements, so that it is possible to reduce a power source voltage to be supplied to the light irradiation substrate. Moreover, according to the aforementioned configuration, it is possible to connect the plurality of light-emitting elements in series in the first direction and connect the plurality of light-emitting elements in parallel in the second direction only with the first electrical conducting patterns provided on a side of the first surface without providing a wiring on the side of the second surface, so that it is possible to reduce costs of manufacturing the light irradiation substrate.

The invention is not limited to each of the embodiments described above, and may be modified in various manners within the scope indicated in the claims and an embodiment achieved by appropriately combining technical means disclosed in each of different embodiments is also encompassed in the technical scope of the invention. Further, by combining the technical means disclosed in each of the embodiments, a new technical feature may be formed.

INDUSTRIAL APPLICABILITY

The invention is able to be suitably used for a light irradiation substrate by which an affected part of a skin of a human being or an animal is irradiated with light.

REFERENCE SIGNS LIST 1 light irradiation substrate
2 wiring (first surface side wiring, first electrical conducting material pattern)
2C cathode wiring (first surface side wiring, first electrical conducting material pattern)
2A anode wiring (first surface side wiring, first electrical conducting material pattern)
2I inter-chip wiring (first surface side wiring, first electrical conducting material pattern)
2CT cathode terminal (terminal unit, first electrical conducting material pattern)
2AT anode terminal (terminal unit, first electrical conducting material pattern)
2CV cathode vertical wiring (first surface side wiring, first electrical conducting material pattern)
2AV anode vertical wiring (first surface side wiring, first electrical conducting material pattern)
3 bonding wire
4 LED chip (light-emitting element)
5 flexible substrate
6 dummy pattern (first electrical conducting material pattern)
7 wiring protection film (protection film)
7a opening
8 LED protective resin dome (protection film)
9 connection hole
10 rear wiring (second surface side wiring)
10C rear cathode wiring (second surface side wiring)
10A rear anode wiring (second surface side wiring)
11 connection part seal
12 external connection unit
12a cathode external connection unit
12b anode external connection unit
13 rear surface reflection film
14 rear surface protection film
15, 51, 52, 53, 54 first electrical conducting material pattern
16, 49 solder
17 bending part
18 bending line
20 silver plating layer
21 insulating isolation groove
22 copper plating layer
30 mouse
31 skin
32 spacer
33 affected part
34 blue-violet light
35 light irradiation substrate with a spacer (light irradiation substrate)
40 sensor unit
41 optical sensor
42 temperature sensor
43 control unit
44 switch

The invention claimed is:

1. A substrate for phototherapy comprising:
a flexible substrate that is insulating;
a first electrical conducting material patterns that is provided on a first surface of the flexible substrate; and
a light-emitting elements that is mounted on at least a part of the first electrical conducting material pattern and is surrounded entirely by the part of the first electrical conducting pattern, wherein
a front surface of the first electrical conducting material patterns is formed of a reflecting material with total light flux reflectance percentage of 80% or more, and area coverage of first electrical conducting material patterns at least in a region surrounded by light-emitting elements is 85% or more of the region.

2. The substrate for phototherapy according to claim 1, further comprising
on a second surface opposite of the first surface of the flexible substrate, a light shielding member that prevents light from leaking out from a side of the second surface.

3. The substrate for phototherapy according to claim 2, further comprising
   on the second surface opposite of the first surface of the flexible substrate, second surface side wirings that are electrically connected to a part of the first electrical conducting material patterns,
   an anode wiring and a cathode wiring as the second surface side wirings,
   an anode external connection unit and a cathode external connection unit, wherein the anode wiring and the cathode wiring connected to an outside, respectively, are connected to the second surface side wirings, and
   connection is made to the anode external connection unit and the cathode external connection unit at positions that are adjacent to each other.

4. The substrate for phototherapy according to claim 3, wherein
   each of the anode external connection unit and the cathode external connection unit that are adjacent to each other is connected to a part of the first electrical conducting material patterns.

5. The substrate for phototherapy according to claim 1, further comprising
   a spacer that separates the light-emitting element from an irradiation target that is irradiated with light emitted by the light-emitting element by a constant distance, wherein
   the spacer transmits light emitted by the light-emitting element, and is flexible.

6. The substrate for phototherapy according to claim 1, wherein
   the first electrical conducting material pattern and the light-emitting element are covered with a wiring protection film.

7. A substrate for phototherapy comprising:
   a flexible substrate that is insulating;
   first electrical conducting material patterns that are provided on a first surface of the flexible substrate; and
   light-emitting elements that are mounted on at least a part of the first electrical conducting material patterns, wherein
   front surfaces of the first electrical conducting material patterns are formed of a reflecting material with total light flux reflectance percentage of 80% or more, and
   area coverage of the first electrical conducting material patterns at least in a region surrounded by the light-emitting elements is 85% or more of the region,
   wherein a dummy pattern is provided in the first surface of the flexible substrate, except for a part on which the first electrical conducting material patterns are placed.

* * * * *